(12) United States Patent
Sullivan et al.

(10) Patent No.: US 9,592,354 B2
(45) Date of Patent: *Mar. 14, 2017

(54) COMBINATION UNIT DOSE DISPENSING CONTAINERS

(75) Inventors: Timothy R. Sullivan, Cedar Park, TX (US); Jeffrey Nelson, Round Rock, TX (US)

(73) Assignee: Mystic Pharmaceuticals, Inc., Austin, TX (US)

( * ) Notice: Subject to any disclaimer, the term of this patent is extended or adjusted under 35 U.S.C. 154(b) by 773 days.

This patent is subject to a terminal disclaimer.

(21) Appl. No.: 13/191,315

(22) Filed: Jul. 26, 2011

(65) Prior Publication Data

US 2011/0277763 A1 Nov. 17, 2011

Related U.S. Application Data

(60) Continuation of application No. 12/694,849, filed on Jan. 27, 2010, now Pat. No. 8,047,204, which is a
(Continued)

(51) Int. Cl.
*A61M 15/00* (2006.01)
*A61M 35/00* (2006.01)
(Continued)

(52) U.S. Cl.
CPC .... *A61M 15/0028* (2013.01); *A61M 15/0031* (2014.02); *A61M 15/0036* (2014.02);
(Continued)

(58) Field of Classification Search
CPC .......... A61M 15/0028; A61M 15/0031; A61M 15/0051; A61M 15/0061; A61M 35/003;
(Continued)

(56) References Cited

U.S. PATENT DOCUMENTS 1,870,558 A 8/1932 Darby
2,105,946 A 1/1938 Lewis
(Continued)

FOREIGN PATENT DOCUMENTS

GB 9125699 12/1991
WO WO94/20408 9/1994
(Continued)

OTHER PUBLICATIONS

PCT/US05/13962, International Search Report, Jan. 31, 2006.
(Continued)

*Primary Examiner* — Chun Cheung
(74) *Attorney, Agent, or Firm* — Vinson & Elkins LLP

(57) ABSTRACT

Dosage forms containing pharmaceutical compositions for use in devices to produce a spray or mist delivery of the compositions include dosage blister compartments and a dispensing blister compartment, wherein crushing of the compartments delivers the compositions in a desired spray pattern. Certain dosage forms include a plurality of dosage chambers each containing a component or a portion of a pharmaceutical composition, the contents of which are mixed or combined just prior to or during administration.

9 Claims, 34 Drawing Sheets

Related U.S. Application Data division of application No. 12/121,644, filed on May 15, 2008, now Pat. No. 7,669,597.

(60) Provisional application No. 60/938,379, filed on May 16, 2007, provisional application No. 60/978,619, filed on Oct. 9, 2007.

(51) Int. Cl.
    *A61F 9/00*           (2006.01)
    *A61J 1/06*           (2006.01)

(52) U.S. Cl.
CPC .... *A61M 15/0051* (2014.02); *A61M 15/0061* (2014.02); *A61M 35/003* (2013.01); *A61F 9/0008* (2013.01); *A61J 1/067* (2013.01); *A61J 1/2024* (2015.05); *A61J 1/2027* (2015.05); *A61M 15/003* (2014.02); *A61M 2202/064* (2013.01)

(58) Field of Classification Search
CPC ............ A61M 15/003; A61M 2202/064; A61J 1/2024; A61J 1/2027; A61J 1/067; A61F 9/0008
USPC ................. 206/531, 219.229; 222/94, 541.2; 128/203.21, 200.14; 604/58, 518, 195
See application file for complete search history.

(56) References Cited

U.S. PATENT DOCUMENTS

| | | |
|---|---|---|
| 2,307,980 A | 1/1943 | Avrett |
| 2,332,799 A | 10/1943 | Hunn |
| 2,442,004 A | 5/1948 | Hayward-Butt |
| 2,706,984 A | 4/1955 | Lipari |
| 2,885,931 A | 4/1955 | McDonald |
| 2,769,443 A | 11/1956 | Dunmire |
| 3,507,277 A | 4/1970 | Altounyan et al. |
| 3,512,524 A | 5/1970 | Drewe |
| 3,888,253 A | 6/1975 | Watt et al. |
| 3,906,950 A | 9/1975 | Cocozza |
| 3,948,264 A | 4/1976 | Wilke et al. |
| 3,949,751 A | 4/1976 | Birch et al. |
| 3,971,377 A | 7/1976 | Damani |
| 4,013,075 A | 3/1977 | Cocozza |
| 4,017,007 A | 4/1977 | Riccio |
| 4,090,642 A | 5/1978 | Baker |
| 4,095,596 A | 6/1978 | Grayson |
| 4,105,027 A | 8/1978 | Lundquist |
| 4,116,195 A | 9/1978 | James |
| 4,206,758 A | 6/1980 | Hallworth et al. |
| 4,423,724 A | 1/1984 | Young |
| 4,623,337 A | 11/1986 | Maurice |
| 4,684,366 A | 8/1987 | Denny et al. |
| 4,750,650 A * | 6/1988 | Ling ........................... 222/632 |
| 4,852,551 A | 8/1989 | Opie et al. |
| 4,896,832 A | 1/1990 | Howlett |
| 4,952,212 A | 8/1990 | Booth et al. |
| 4,966,581 A | 10/1990 | Landau |
| 4,995,385 A | 2/1991 | Valentini et al. |
| 5,048,727 A | 9/1991 | Vlasich |
| 5,152,284 A | 10/1992 | Valentini et al. |
| 5,154,710 A | 10/1992 | Williams |
| 5,207,217 A | 5/1993 | Cocozza et al. |
| 5,219,101 A | 6/1993 | Matkovich et al. |
| 5,273,190 A | 12/1993 | Lund |
| 5,287,850 A | 2/1994 | Haber et al. |
| 5,307,953 A | 5/1994 | Regan |
| 5,327,883 A | 7/1994 | Williams et al. |
| 5,337,740 A | 8/1994 | Armstrong et al. |
| 5,379,763 A | 1/1995 | Martin |
| 5,411,175 A | 5/1995 | Armstrong et al. |
| 5,425,480 A | 6/1995 | Rabenau et al. |
| 5,431,155 A | 7/1995 | Marelli |
| 5,433,343 A | 7/1995 | Meshberg |
| 5,469,989 A | 11/1995 | Graf et al. |
| 5,492,112 A | 2/1996 | Mecikalski et al. |
| 5,497,763 A | 3/1996 | Lloyd et al. |
| 5,524,419 A | 6/1996 | Shannon |
| 5,529,059 A | 6/1996 | Armstrong et al. |
| 5,547,131 A | 8/1996 | Brace |
| 5,616,128 A | 4/1997 | Meyer |
| 5,643,211 A | 7/1997 | Sadowski et al. |
| 5,683,361 A | 11/1997 | Elk et al. |
| 5,715,810 A | 2/1998 | Armstrong et al. |
| 5,715,811 A | 2/1998 | Ohki et al. |
| 5,769,278 A | 6/1998 | Kummer et al. |
| 5,810,004 A | 9/1998 | Ohki et al. |
| 5,813,570 A | 9/1998 | Fuchs et al. |
| 5,881,721 A | 3/1999 | Bunce et al. |
| 5,896,855 A | 4/1999 | Hobbs et al. |
| 5,901,703 A | 5/1999 | Ohki et al. |
| 5,921,236 A | 7/1999 | Ohki et al. |
| 5,924,417 A | 7/1999 | Braithwaite |
| 5,944,222 A | 8/1999 | Fuchs et al. |
| 5,950,619 A | 9/1999 | van der Linden et al. |
| 5,964,417 A | 10/1999 | Amann et al. |
| 5,970,974 A | 10/1999 | Van Der Linden et al. |
| 6,101,790 A | 8/2000 | Mori et al. |
| 6,109,479 A | 8/2000 | Ruckdeschel |
| 6,116,238 A | 9/2000 | Jackson et al. |
| 6,123,068 A | 9/2000 | Lloyd et al. |
| 6,135,755 A | 10/2000 | Zeiter et al. |
| 6,138,439 A | 10/2000 | McMahon et al. |
| RE37,047 E | 2/2001 | Py |
| 6,186,141 B1 | 2/2001 | Pike et al. |
| 6,321,942 B1 | 11/2001 | Krampen et al. |
| 6,367,473 B1 | 4/2002 | Kafer |
| 6,382,465 B1 | 5/2002 | Greiner-Perth |
| 6,425,888 B1 | 7/2002 | Embleton et al. |
| 6,443,152 B1 | 9/2002 | Lockhart et al. |
| 6,446,839 B1 | 9/2002 | Ritsche |
| 6,461,322 B1 | 10/2002 | Ritsche |
| 6,470,650 B1 | 10/2002 | Lohwasser |
| 6,481,645 B1 * | 11/2002 | Taylor-McCune et al. .. 239/461 |
| 6,484,715 B1 | 11/2002 | Ritsche et al. |
| 6,530,371 B2 | 3/2003 | Jansen et al. |
| 6,543,448 B1 | 4/2003 | Smith et al. |
| 6,626,379 B1 | 9/2003 | Ritsche et al. |
| 6,644,309 B2 | 11/2003 | Casper et al. |
| 6,679,248 B2 | 1/2004 | Stadelhofer |
| 6,705,313 B2 | 3/2004 | Niccolai |
| 6,708,846 B1 | 3/2004 | Fuchs et al. |
| 6,725,857 B2 | 4/2004 | Ritsche |
| 6,726,665 B1 | 4/2004 | Embleton et al. |
| 6,730,066 B1 | 5/2004 | Bennwik et al. |
| 6,732,732 B2 | 5/2004 | Edwards et al. |
| 6,758,837 B2 | 7/2004 | Peclat et al. |
| 6,772,915 B2 | 8/2004 | Helmlinger |
| 6,782,887 B2 | 8/2004 | Sullivan |
| 6,877,672 B2 | 4/2005 | Stihl |
| 6,889,690 B2 | 5/2005 | Crowder et al. |
| 6,929,005 B2 | 8/2005 | Ritsche et al. |
| 6,957,909 B1 | 10/2005 | Dingeldein et al. |
| 7,097,075 B2 * | 8/2006 | Peuker et al. .................. 222/94 |
| 7,235,063 B2 | 6/2007 | D'Antonio et al. |
| 7,270,127 B2 | 9/2007 | Lockhart et al. |
| 7,669,597 B2 | 3/2010 | Sullivan et al. |
| 7,963,089 B2 | 6/2011 | Nelson et al. |
| 8,047,204 B2 | 11/2011 | Sullivan et al. |
| 2001/0007327 A1 | 7/2001 | Ritsche et al. |
| 2003/0105430 A1 | 6/2003 | Lavi et al. |
| 2003/0199832 A1 | 10/2003 | Greiner-Perth et al. |
| 2004/0215133 A1 | 10/2004 | Weber |
| 2005/0000518 A1 | 1/2005 | Dunkley et al. |
| 2005/0016533 A1 | 1/2005 | Schuler et al. |
| 2005/0022813 A1 | 2/2005 | Alston |
| 2005/0048003 A1 | 3/2005 | Ohki et al. |
| 2005/0051166 A1 | 3/2005 | Glusker et al. |
| 2005/0056280 A1 | 3/2005 | Alston et al. |
| 2005/0081852 A1 | 4/2005 | Rangachari |
| 2005/0150492 A1 | 7/2005 | Dunkley et al. |
| 2006/0237009 A1 | 10/2006 | Jones |

(56) References Cited

U.S. PATENT DOCUMENTS

| | | | |
|---|---|---|---|
| 2006/0283728 A1* | 12/2006 | Patrick et al. | 206/229 |
| 2007/0051362 A1 | 3/2007 | Sullivan et al. | |
| 2008/0177246 A1 | 7/2008 | Sullivan et al. | |
| 2008/0283439 A1 | 11/2008 | Sullivan et al. | |
| 2010/0331765 A1 | 12/2010 | Sullivan et al. | |
| 2011/0247305 A1 | 10/2011 | Nelson | |
| 2011/0277763 A1 | 11/2011 | Sullivan et al. | |

FOREIGN PATENT DOCUMENTS

| | | |
|---|---|---|
| WO | 9600050 | 1/1996 |
| WO | 9723177 | 7/1997 |
| WO | WO2005/032998 | 4/2005 |
| WO | 2005102058 A2 | 11/2005 |
| WO | WO2005/102058 | 11/2005 |
| WO | WO2008/086413 | 7/2008 |
| WO | WO2008/144439 | 11/2008 |
| WO | WO2009/036422 | 3/2009 |

OTHER PUBLICATIONS

Abelson, M.B. and Rosner, Sarah A., "Prevent Drugs From Going Missing in Action," Review of Opthalmology, Jun. 15, 2003, 10:6, pp. 96-98.

Abelson, M.B. and Shapiro, A., "Hitting the Bull's-eye With Drug Delivery," Review of Opthalmology, Jul. 15, 2003, 10:7, pp. 82-84.

Aurora, Jack, "Nasal Delivery, Articles: Development of Nasal Delivery System: A review," Drug Delivery Technology, 2002, 2(7); pp. 70-73.

Chiarello, Kaytynn, "Bi-directional Nasal Device Delivers Drug on Exhalation," In the Field Pharmaceutical Science & Technology News, Sep. 2004, pp. 15-18.

Ingelheim. Bochringer, "Aseptic Production of Pharmaceuticals in Boehringer Ingelheim Using Blow-Fill-Seal Technology," Technology & Services, Business Briefing: Pharmatech, 2003, pp. 1-3.

Lofgren, Anders et al., "Blow-Fill-Seal Pharmaceutical Packaging—Towards Safe and Convenient Medical Containers," Business Briefing: Pharma Outsourcing, Jan. 2004, pp. 78-81.

Jenevieve B. Polin, "Blow-Fill-Seal Technology for Unit Dosing," Pharmaceutical & Medical Packaging News, Sep. 2003.

O'Riordan, Thomas G., "Inhaled Antimicrobial Therapy: From Cystic Fibrosis to the Flu," Respiratory Care, Jul. 2000, vol. 45, No. 7, pp. 836-845.

Saettone, Marco F., "Progress and Problems in Opthalmic Drug Delivery," Business Briefing: Pharmatech, May 2003, pp. 167-171.

Salt, Alec N., "Simulation of Methods for Drug Delivery to the Cochlear Fluids," Felix D. Oestreicher, e. (eds.): Rational Pharmacotherapy of the Inner Ear. Adv. Otorhinolaryngol. Basel, Karger, 2002, vol. 59, p. 140.

Guidance for Industry, "Container Closure Systems for Packaging Human Drugs and Biologies," U.S. Dept. of Health and Human Services, FDA, CDER, CBER, May 1999.

Guidance for Industry, "Sterile Drug Products Produced by Aseptic Processing—Current Good Manufacturing Practice," U.S. Dept. of Health and Human Services, FDA, CDER, CBER, ORA, Sep. 2004.

* cited by examiner

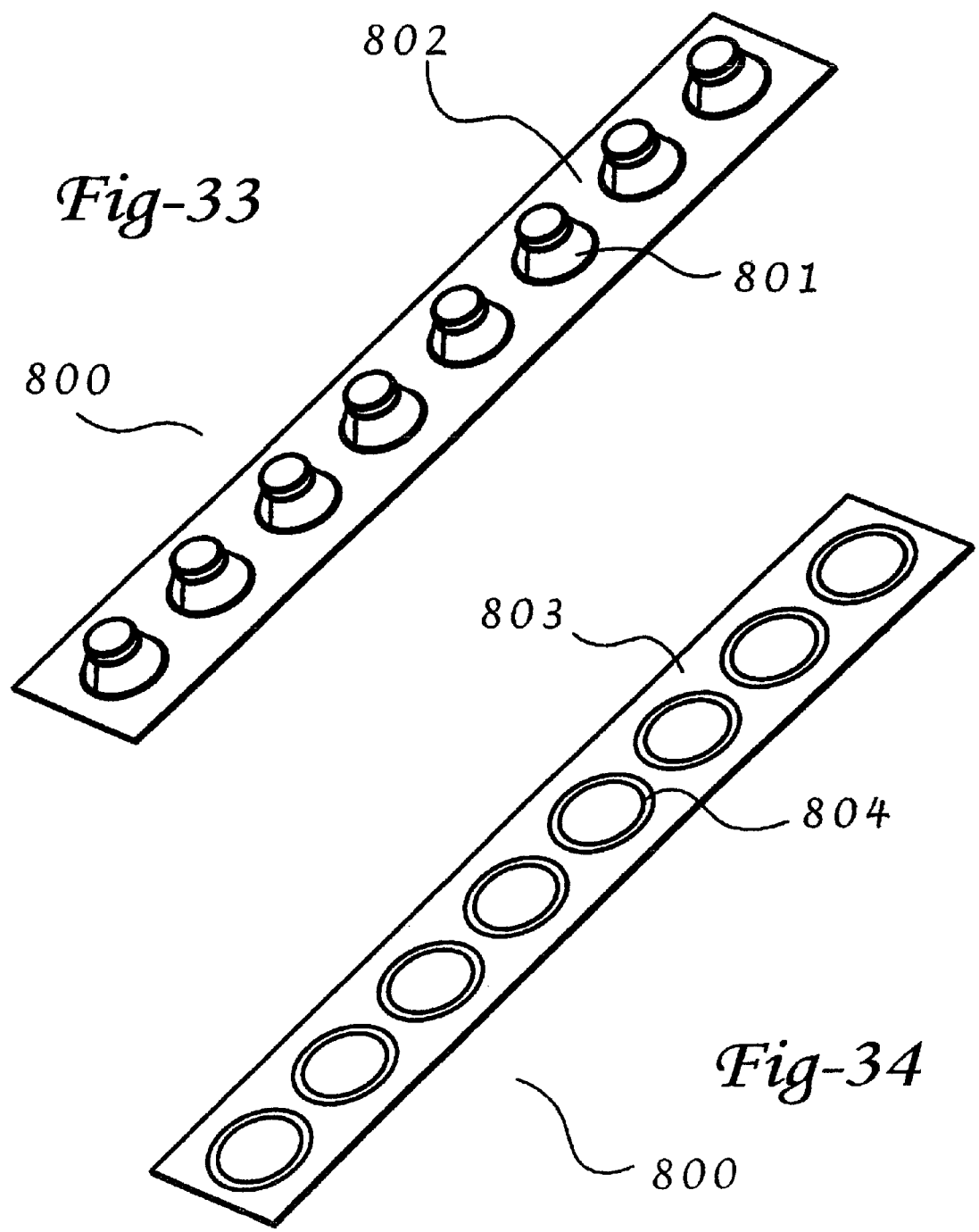

COMBINATION UNIT DOSE DISPENSING CONTAINERS

CROSS-REFERENCE TO RELATED APPLICATIONS

This application is a continuation application of U.S. Ser. No. 12/694,849, filed Jan. 27, 2010; which is a divisional application of U.S. Ser. No. 12/121,644, filed May 15, 2008, now U.S. Pat. No. 7,669,597; and also claims priority to U.S. Provisional No. 60/978,619, filed Oct. 9, 2007, and U.S. Provisional No. 938,379, filed May 16, 2007, each of which are hereby incorporated by reference in their entirety for all purposes.

STATEMENT REGARDING FEDERALLY SPONSORED RESEARCH OR DEVELOPMENT

N/A

BACKGROUND OF THE INVENTION

There are a growing number of drugs and vaccines for which the most effective or most convenient method of administration is by delivery of a spray or mist. A variety of devices are known for delivering a controlled amount of a pharmaceutical preparation in a spray or mist to the nose, eye, ear, lungs, or throat of a user, or for topical delivery of an active agent. Various devices for delivery of a liquid or even a powdered formulation include a measured amount of a pharmaceutical composition contained in a crushable ampul, blister or other dosage form that is forced against a penetrating device during use, to pierce the dosage form to release the contents.

Although a pre-measured dosage form is a convenient way to store and then deliver a measured dose as needed, not all drugs can be stored in this manner prior to use. For example, certain active agents are unstable when combined with a liquid carrier, and certain active agents are required to be mixed just prior to administration. Many drugs, including protein drugs and vaccines may be more stable in lyophilized form and need to be hydrated just prior to use for optimal activity.

There is a need, therefore, for storage and delivery devices for measured dosages of active agent(s) in which the components of the agent(s) can be stored in a separate chamber and then mixed with a liquid or another active agent just prior to use.

BRIEF SUMMARY OF INVENTION

The present disclosure provides drug or pharmaceutical dosage forms for use in delivery devices that deliver a stream, drops, spray or mist in a desired volume and spray The present disclosure provides drug or pharmaceutical dosage forms for use in delivery devices that deliver a stream, drops, spray or mist in a desired volume and spray geometry to a human or non-human animal. The dosage forms can be used, for example, to deliver a measured dose of a pharmaceutical or medical composition to the nasal passages, to the eye, to the mouth, into the ear, into the lungs, into the throat, or to a topical location of a user. In preferred embodiments a predetermined quantity of a pharmaceutical or medical composition comprising a fluid or a solid such as a powder or a lyophilized agent is contained in, or produced in an ampul or blister dosage form that is crushed by a plunger with sufficient force to drive the dosage form against a piercing mechanism, piercing the dosage form and forcing the liquid or solid contents from the dosage form and through a delivery channel into a spray to be directed to the user. A predetermined quantity refers, in most instances, to a single dose of medication or a pharmaceutical or medical composition, and in certain embodiments to a prescribed dose. A predetermined quantity of fluid or solid dosage form may also be a partial dose when delivery of a dose is administered in two or more spray events.

Any pharmaceutical agent that is deliverable in a powder, lyophilized, or liquid form is contemplated in the present disclosure, including but not limited to antibiotics, antipyretics, anti-inflammatories, biologics, vitamins, co-factors, enzymes, inhibitors, activators, nutrients, vaccines including DNA based killed or live virus or microorganisms, nucleic acids, proteins, peptides, antibodies, peptide mimetics, or other agents or pharmaceutical compositions known in the art. The pharmaceutical compositions are in the form of a liquid, a powder, a lyophilized agent, or any combination thereof, and include one or more active agents, which may be combined or mixed with pharmaceutically acceptable carriers, solvents, diluents, preservatives, surfactants, salts, adjuvants, viscosity agents, buffers, chelators, or other ingredients known to those in the art as needed.

In preferred embodiments when the dosages are intended to be delivered or administered to a human subject, the preferred agents, e.g., matrix materials, therapeutic agent, active agent, plasticizer, surfactant, and functional excipients of the present disclosure are pharmaceutically acceptable materials. As used herein, "pharmaceutically acceptable carrier" or "pharmaceutically acceptable materials" includes any and all solvents, dispersion media, coatings, antibacterial and antifungal agents, isotonic and absorption delaying agents, absorption enhancing agents and the like. The use of such media and agents for pharmaceutically active agents is well known in the art. Except insofar as any conventional media or agent is incompatible with the active agent, its use in the therapeutic compositions is contemplated. Supplementary active agents can also be incorporated into the compositions. The phrase "pharmaceutically acceptable" also refers to molecular entities and compositions that do not produce an allergic or similar untoward reaction when administered to a human or animal.

This present disclosure can be described in certain embodiments as a dosage form for delivery of a pharmaceutical composition, in which the dosage form includes a first dosage chamber containing a first component of the pharmaceutical composition, a second dosage chamber containing a second component of the pharmaceutical composition, and a dispensing chamber that includes a piercable membrane. The second dosage chamber and the dispensing chamber may be two separate chambers, or the same chamber. The piercable membrane is a section of the membrane that is designed to be pierced by a piercing mechanism or device. The piercable membrane may include an area that is weakened by scoring, or thinned, effective to inhibit production of loose pieces of the membrane during use as it is penetrated, and to promote a seal of the pierced membrane to outer walls of the piercing tip. The dosage form also comprises a seal, for example first delamination seal, that prevents mixing of the contents of the first dosage chamber with the contents of the second dosage chamber, and may comprise a second delamination seal that prevents mixing of the contents of the second chamber with the dispensing chamber. The dosage form may further comprise a permanent seal, wherein the permanent seal surrounds the outer perimeter of all the chambers, and in which the first and second delamination seals have less adhesion than the permanent seal, such that the first and second delamination seals delaminate under significantly less pressure than the permanent seal.

As used herein, the term "dosage chamber", which encompasses the term "dosage blister chamber", refers to a compartment of the disclosed dosage forms that contain a component or a portion of the final pharmaceutical composition. A dosage chamber can contain a liquid or a solid composition, to be mixed with other components to form the final pharmaceutical composition when the contents of the chambers are combined during or just prior to administration. A "dispensing chamber", which encompasses the term "dispensing blister chamber", refers to a chamber that includes a piercable membrane and can include an internal piercing mechanism. Delamination zones are seals that are designed to break or delaminate when pressure is applied to the chambers so that the contents of the chambers can be mixed.

Certain dosage forms of the disclosure have two dosage chambers separated by a delamination zone, or in certain embodiments by a high vapor barrier material such as aluminum foil, for example. Embodiments also include dosage forms with three, four, five, or more dosage chambers, the contents of all of which are mixed as the pharmaceutical composition is delivered. The chambers can contain liquids or solids in any combination, however, in preferred embodiments, the final pharmaceutical composition is in liquid form. In certain embodiments one or more or even all of the dosage chambers can contain the same composition, or aliquots portions of the same composition when the volume of a dose is too large to fit within a single dosage chamber. It is an aspect of the disclosure that the dosage chambers are separated from each other during storage by delamination zones, or by membranes that can be pierced by a piercing device or burst by pressure, such that the barrier is removed when pressure is applied to the chambers in a delivery device, and that the final delamination or designed membrane failure is effective to allow the completed composition to enter the dispensing chamber for discharge to the site of treatment.

In certain embodiments the dispensing chamber includes an internal piercing device. It is understood that the disclosed devices can also be designed for use with an external piercing mechanism that is part of the delivery device. The internal piercing device offers several important advantages to the dosage form with respect to manufacturing, as well as maintaining the sterility of the dispensing nozzle until the pharmaceutical composition is dispensed through the nozzle. Preferably the internal piercing device is an integrated piercer nozzle dispensing system.

The dosage forms of the disclosure are described, therefore, in certain embodiments as including a dispensing blister chamber that contain a piercing device, wherein the piercing device is a substantially hollow, elongate member with a base end and a piercing tip opposite the base end and providing a discharge nozzle. In certain embodiments the dispensing blister conforms to at least the base end of the piercing device effective to support and hold the piercing device in place during manufacture and use of the dosage form. The piercing devices include one or more inlet openings on or near the base end and an internal conduit providing fluid communication between the one or more inlet ports and the discharge nozzle; and the surface of the internal conduit comprises structural features such as contours, steps, flutes, ribs, constrictions, or a combination thereof to control the spray pattern and droplet size of a fluid forced through the piercing device. It is a further aspect of the disclosure that the inlet openings provide a fluid path from the interior of the dispensing blister chamber into the internal conduit that comprises one or more 90° bends, and that the combination of right angle turns and the structural features of the internal conduit create vortices in the fluid as it is forced through the piercing mechanism.

It is understood that certain pharmaceutical compositions may require additional mixing prior to administration. This can be accomplished by a user shaking a delivery device prior to the final discharge step, or it can be provided by the structure of the final delamination zone. For example, certain embodiments of the disclosure include a delamination seal separating the dosage blister chambers from the dispensing blister chamber that includes structural features to promote mixing of the contents of the dosage blister chambers. Preferred structures include, but are not limited to one or more curves, a serpentine shape, constrictions, or a combination thereof. The mixing can also be accomplished by the configuration of the piercing nozzle. For example, the nozzle configurations can further control the velocity, pressure, pattern, distribution, aim, and plume geometry of the released fluid or powder.

In certain embodiments, therefore, the disclosure may also be described as a piercing nozzle for dispensing a fluid or solid composition from a dosage form with a particular volume, in a controlled spray pattern and droplet size. The nozzle includes a substantially elongate member with an inlet end and a discharge end, an internal channel connecting the inlet end and the discharge end in fluid communication, one or more inlet openings in the inlet end, a discharge opening in the discharge end, and features on the internal chamber surface to control the spray pattern and droplet size of a fluid forced through the nozzle. The inlet ports are designed to provide a fluid path into the internal channel that includes one or more right angle turns. The inlet ports can also be designed to produce a vortex in the liquid or solid composition as it is forced through the ports. Features in the internal channel can also include, but are not limited to, steps, flutes, ribs, constrictions, contours, and related structures to produce the desired droplet size and spray geometry. In certain embodiments, the piercing tip may be on the discharge end of the elongated member, or on the inlet end. The piercing nozzle can be contained in a dosage form. The disclosure includes, therefore, a dosage form that comprises the piercing nozzle and a pharmaceutical composition.

In certain embodiments the present disclosure can be described as an internally pierced dosage form that includes a substantially dome shaped, flexible blister, a substantially round piercable surface sealed to the base of the dome-shaped blister, and an internal chamber containing a piercing nozzle as described herein and a liquid composition. In certain embodiments the piercing nozzle includes a base and a piercing end, and wherein the base is attached to the dome shaped blister and the piercing end is proximate the piercable surface.

Certain aspects of the disclosure are included so that the dosage forms can be used with particular types of delivery devices. As such, in certain embodiments, any of the disclosed dosage forms can be manufactured on a strip or disk to be dispensed sequentially. In this way, multiple dosages can be included in a single package. Dosage forms are also designed to be used with delivery devices that perform the steps of: compressing the dosage blister chambers, effective to delaminate the delamination seals between the dosage blister chambers and to allow the contents of the dosage blister chambers to mix or combine; compressing the dispensing chamber effective to drive the piercing tip through the membrane; and further compressing the dosage blister chambers effective to delaminate the delamination seal separating the dosage blister chambers from the dispensing blister chamber and to expel the mixed or combined pharmaceutical composition through the piercing device and out the discharge nozzle.

Another embodiment of the present disclosure is a dosage form for delivery of a pharmaceutical composition, including a first dosage blister chamber containing a first component of the pharmaceutical composition; a second dosage blister chamber containing a second component of the pharmaceutical composition; and a dispensing blister chamber comprising a piercable, pressure burstable or mechanically weakened membrane. This dosage form further includes a vapor barrier membrane separating the first dosage blister chamber from the second dosage blister chamber; and a delamination seal, wherein the delamination seal prevents mixing of the contents of the dosage blister chambers with the dispensing chamber. In preferred embodiments this dosage form is formed of a sheet material that has three layers in a sandwich form, with two outer layers and an inner layer. The first outer layer is preferably a high vapor barrier material that forms a membrane layer of the dosage form; the inner layer is also a high vapor barrier material that forms the diaphragm of the first dosage blister chamber and separates the contents of the first dosage blister chamber from the contents of the second dosage blister chamber; and a second outer layer that is a flexible diaphragm material that forms the diaphragm of the second dosage blister chamber and the dispensing blister chamber. In certain embodiments the high vapor barrier material separating the contents of the first dosage blister chamber from the contents of the second dosage blister chamber can be thinned or scored to produce breakage at a specific location when pressure is applied to the dosage blister chambers. In alternative embodiments there can also be a piercing device positioned in one of the dosage blister chambers effective to pierce the high vapor barrier material and allow the contents of the dosage blister chambers to mix when sufficient pressure is applied to the dosage blister chambers.

The disclosed internally pierced dosage forms can also be designed for dispensing devices that require a smaller footprint or diameter of the dosage form, such as in intranasal dispensing devices that must actually enter the nostril of a user, for example. In certain embodiments, therefore, a swaging, or pressure forming process is employed to fold back the seal flange of the dosage form, producing a significantly smaller diameter package.

Certain embodiments of the disclosure, therefore, include dosage forms in which two or more components are mixed just prior to dispensing. Such a dosage form can include a blister and a membrane, where the blister is divided into two or more chambers. The chambers are divided by seals that are less adhesive than the primary seal that surrounds the circumference of the total blister. In this embodiment, each chamber contains a solid or liquid portion of the final dose to be mixed, and preferably at least one chamber contains a liquid such that the final mixture is in liquid form. It is an aspect of this embodiment that the contents of one chamber is forced into the interior of an adjacent chamber where the two components are mixed. This is accomplished by applying a force to the first chamber that is sufficient to break the less adhesive seal between chambers without breaking the primary circumferential seal around the blister, and crushing the first chamber to force the contents to enter the second chamber under pressure. The second chamber can be composed of a flexible blister or diaphragm material with the top inverted to minimize the volume of the second chamber prior to mixing. Breaking the seal and forcing the contents of the first chamber into the second chamber causes the top of the chamber to pop up or expand to accommodate the contents of both chambers. The second chamber, that contains or is adjacent to a piercing mechanism is then crushed by a plunger to dispense the mixed composition. The multi-chambered dosage form for mixing components prior to dispensing can be essentially doughnut shaped, with one or more chambers encircling or partially encircling a central chamber, or they may be positioned in a side by side arrangement or even stacked.

In certain embodiments, a dosage form can also include three chambers, in which a first chamber contains a liquid or powder to be mixed with a liquid or powder contained in a second chamber, with preferably at least one component being liquid. In this embodiment, the dosage form includes a third, dispensing chamber into which the contents of the two chambers are delivered and then dispensed. A three chambered mixing dispenser can include two plungers, a first that crushes the dispensing chamber against the piercing mechanism, releasing the air from the chamber without compromising the sterility of the dosage. Another plunger presses the first chamber, forcing the contents of the first chamber through a delamination zone and into a second chamber, mixing or combining the contents of the dosage chambers. As the second piston continues to travel, completely crushing the first and second chambers, the mixed composition is forced into and through the dispensing chamber and out the discharge nozzle in a desired spray pattern. The step between mixing or combining the components and discharging the composition through the discharge nozzle may occur rapidly, or may include a delay to allow the components to mix or combine sufficiently prior to discharge.

The present disclosure can also be described, therefore, as a method for dispensing a pharmaceutical composition comprising two components, wherein the two components are mixed in the dosage form prior to dispensing. The method includes providing a multi chambered dosage form where a first component is contained in a first, crushable chamber and a second component is contained in a second, crushable chamber, and a dispensing chamber that contains an internal piercing mechanism and a discharge outlet, where the first and second chamber are separated by an adhesive seal. The method further includes providing a mechanical pressure to crush the crushable chambers, breaking the adhesive seal and forcing the contents of the crushable chambers together and forcing the contents of the chambers through the piercing mechanism and out the discharge outlet; where preferably at least one of the components is a liquid.

Throughout this disclosure, unless the context dictates otherwise, the word "comprise" or variations such as "comprises" or "comprising," is understood to mean "includes, but is not limited to" such that other elements that are not explicitly mentioned may also be included. Further, unless the context dictates otherwise, use of the term "a" or "the" may mean a singular object or element, or it may mean a plurality, or one or more of such objects or elements.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 33 is a perspective view of a blister strip of dosage forms for use in a multi-dose dispenser.

FIG. 34 is a bottom view of the strip shown in FIG. 33.

DETAILED DESCRIPTION

Preferred embodiments of the present disclosure are directed to dosage forms that contain a measured dose of one or more pharmaceutically active agents and a piercable section such that the dosage form can be pierced to release the contents under pressure. When using the term "under pressure" in the disclosure, it is understood that the pressure is typically an externally applied pressure rather than internal pressure within the dosage form itself. In typical operation, a plunger, lever, ram, wheel, or some other mechanical device contacts the dosage form with sufficient force to crush the dosage form against a piercing member and force the contents out of the opening. The piercing member can be either an external piercing member such as a needle, or the piercing member can be contained within the dosage form or ampul. The dosage form may be generated using methods well known to those of skill in the art, including, for example, form fill seal technology or blow fill seal technology. The form-fill-seal process can be used to create a blister, for example a blister pack, from rolls of flat sheet or film, filled with the pharmaceutically active agent, and closed or sealed on the same equipment. This process involves a formed base which has the cavity in which the pharmaceutically active agent, or an agent that may be mixed or combined with a pharmaceutically active agent, is placed, and a lidding, for example of foil, through which the agent is dispensed out of the blister. Blow fill seal technology involves forming, filling, and sealing a dosage form in a continuous process in a sterile enclosed area inside a machine.

Figure 1:
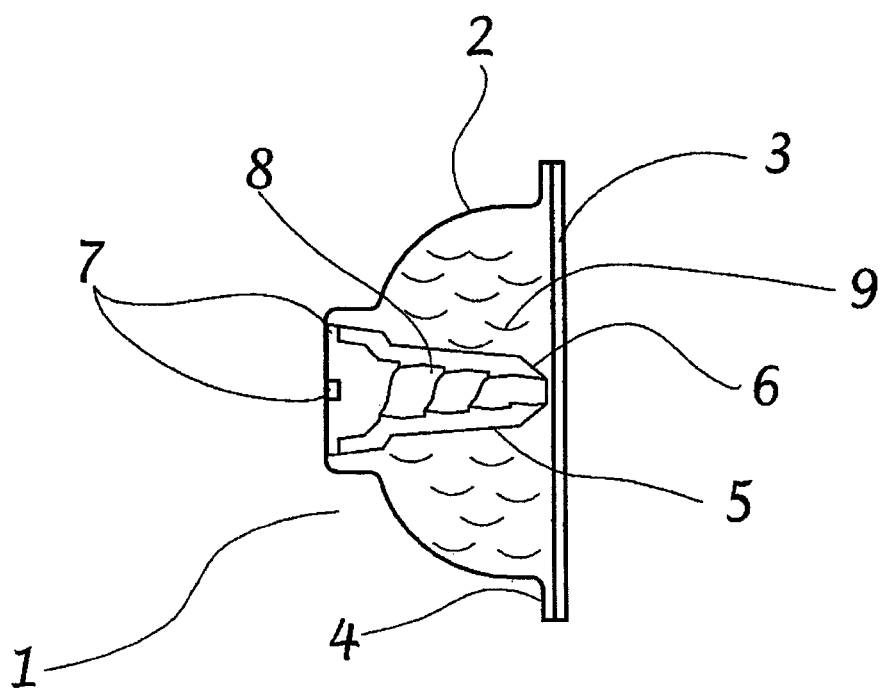
FIG. 1 is an embodiment of a dosage form with an internal piercing mechanism.

An example of a dosage form with an internal piercing member is shown in FIG. 1. The dosage form in FIG. 1 is a blister dosage form 1 that includes a diaphragm 2 formed into a dome shape and a membrane 3 sealed to the diaphragm 2 along the seal area 4. Sealed within the blister dosage form 1 are a piercing nozzle 5 and a liquid composition 9.

Figure 2:
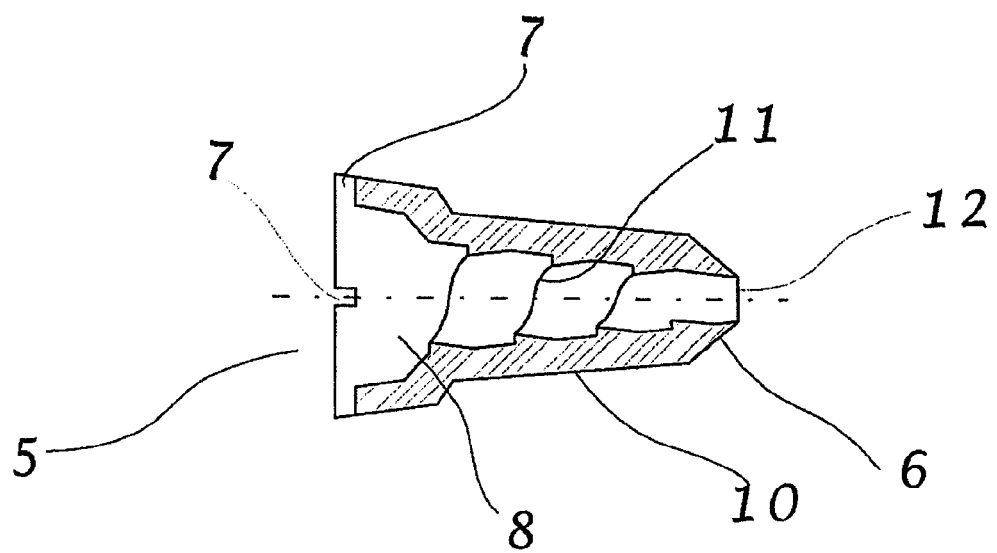
FIG. 2 is an embodiment of a piercing mechanism.

The piercing nozzle of FIG. 1 is also shown in FIG. 2. This example of a piercing nozzle 5 has tapered sides 10 and an inner chamber 8 that connects inlet ports 7 to a discharge port 12. The inner chamber 8 can contain internal contours 11 and other structures on the interior walls of the inner chamber 8. The contours and other structures are designed to influence the flow of the fluid or solid agent 9. Different nozzle configurations are created for specific applications to cause the fluid or solid agent to exit the discharge port 12 in a spray, mist or stream, depending on the needs of a specific medication or application.

Figure 3:
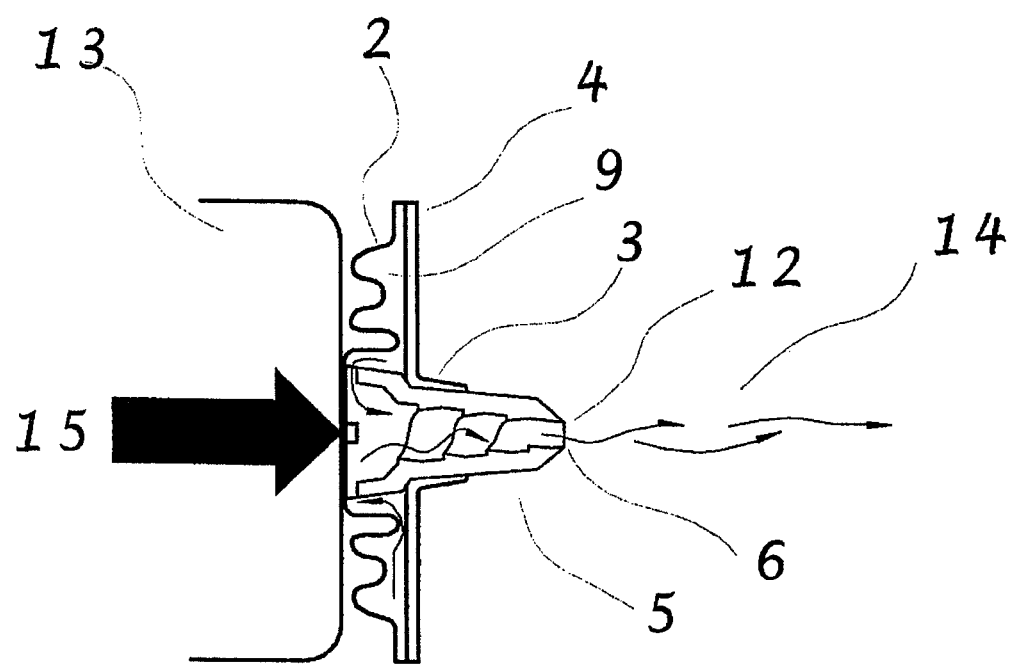
FIG. 3 demonstrates an embodiment of a dosage form with an internal piercing mechanism during administration of the contents.

A blister dosage form is shown during use in FIG. 3. When the dose is to be administered, the dosage form is placed in a device designed to administer the pharmaceutical agent to a particular location, such as in the eye, ear, nose, mouth, lungs or skin of a user, for example. The device may administer the pharmaceutical agent through oral, peroral, enteral, parenteral, pulmonary, rectal, otic, topical, nasal, vaginal, lingual, direct injection, intravenous, intraarterial, intracardial, intradermal, intramuscular, intraperitoneal, intracutaneous, intraocular, ophthalmic, intranasal, intrapleural, intrathecal, intratumor, intrauterine, orthotopic, transdermal, buccal, and subcutaneous or other routes of delivery. Many such devices include a firing mechanism that drives a ram against the dosage form with an explosive force. Examples of such devices are described in pending U.S. Provisional Application No. 60/853,328, incorporated herein in their entirety by reference. The results of this action are demonstrated in FIG. 3, in which a force in the direction 15 is applied with a plunger 13 to the back of the domed diaphragm 2. The piercing tip 6 has penetrated the membrane 3 and the liquid medication 9 has flowed into the inner chamber 8 through the inlet ports 7, out the discharge port 12 and been dispensed in a discharge pattern 14. The piercing tip 6 and tapered sides 10 of the piercing nozzle 5 cause the membrane 3 to seal tightly around the piercing nozzle 5 forcing the medication 9 to flow out the discharge port 12.

Figure 4:
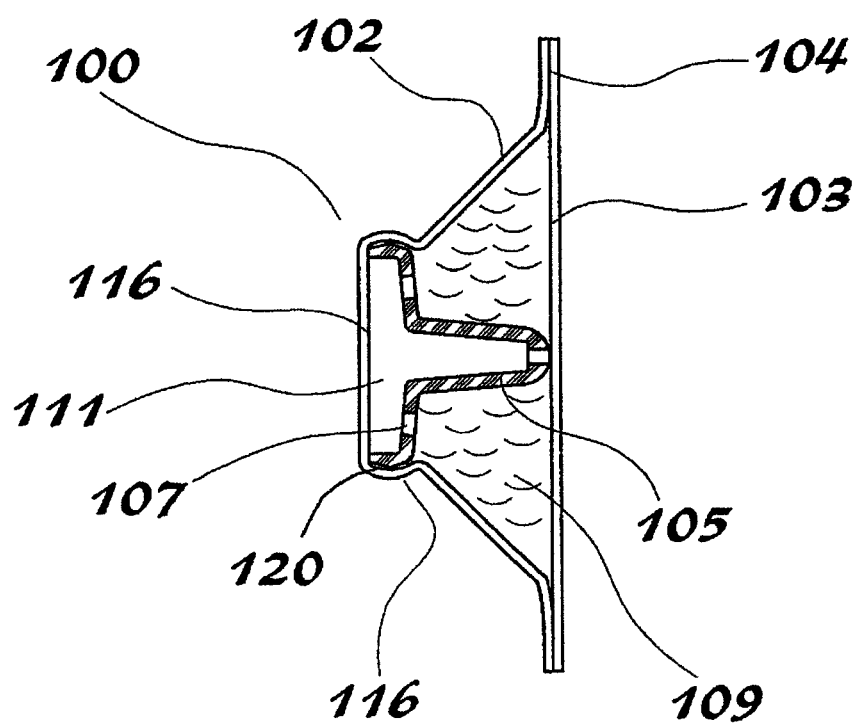
FIG. 4 is an embodiment of a dosage form with an internal piercing mechanism.

Another embodiment of a blister dosage form 100 is shown in FIG. 4. This version has the inlet ports 107 on the same side of the piercing nozzle 105 as the discharge port 112. This configuration forces the components 109 to flow through two 90° bends during dispensing. Forcing the liquid or solid agent to flow through this series of bends in conjunction with the contours 111 in the inner chamber 108 control the discharge pattern 114. In blister dosage form 100 a portion 116 of diaphragm 102 is formed to conform to the shape of the base 120 of the piercing nozzle. The diaphragm provides support for and holds the piercing nozzle 105 in place during assembly and during dispensing. Thus, the diaphragm functions to capture the piercing nozzle and hold it in place through manufacture and actual use.

Figure 5:
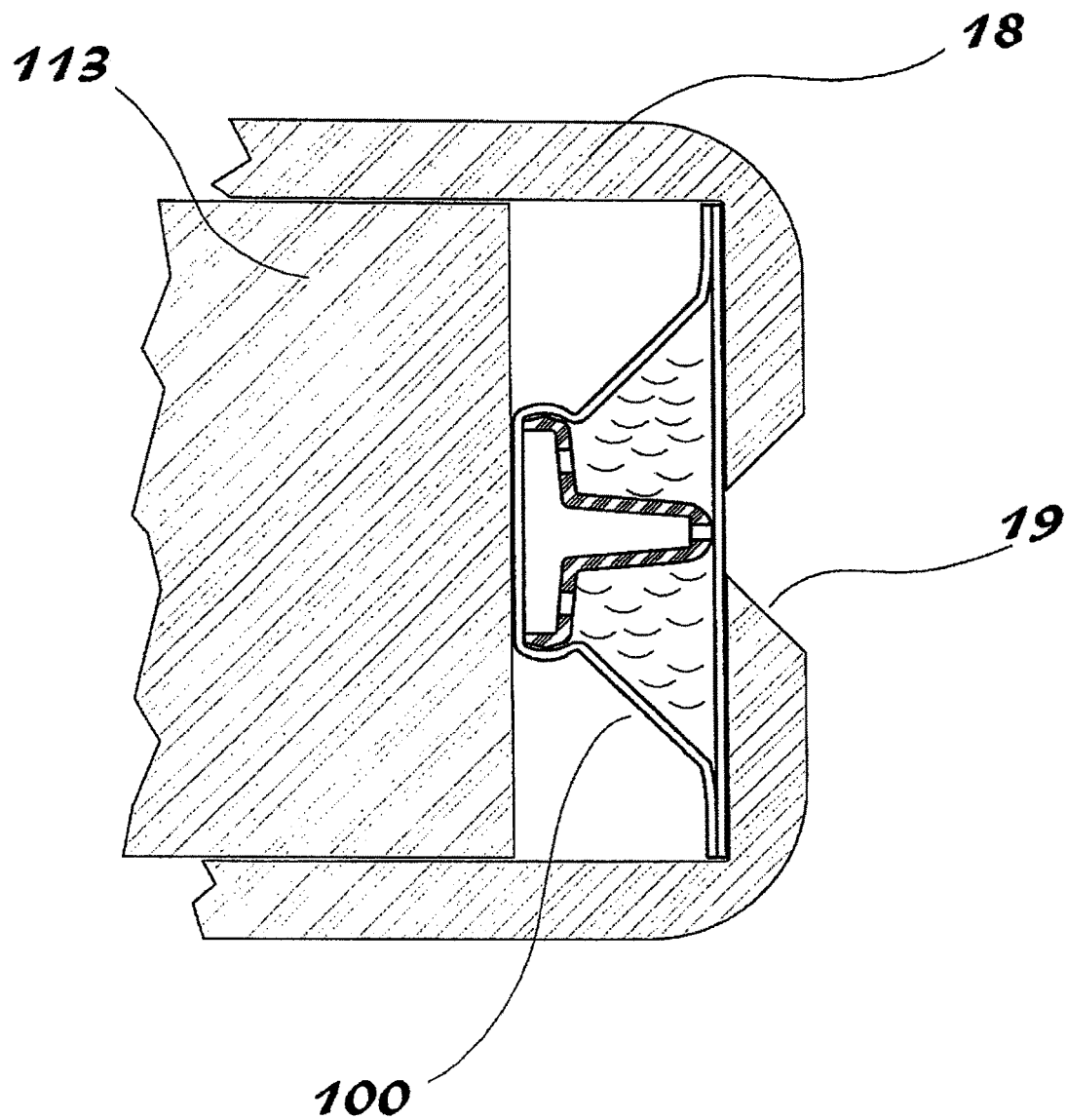
FIG. 5 is a view of the embodiment of FIG. 4 in the housing of a device for administering the dosage.
Figure 6:
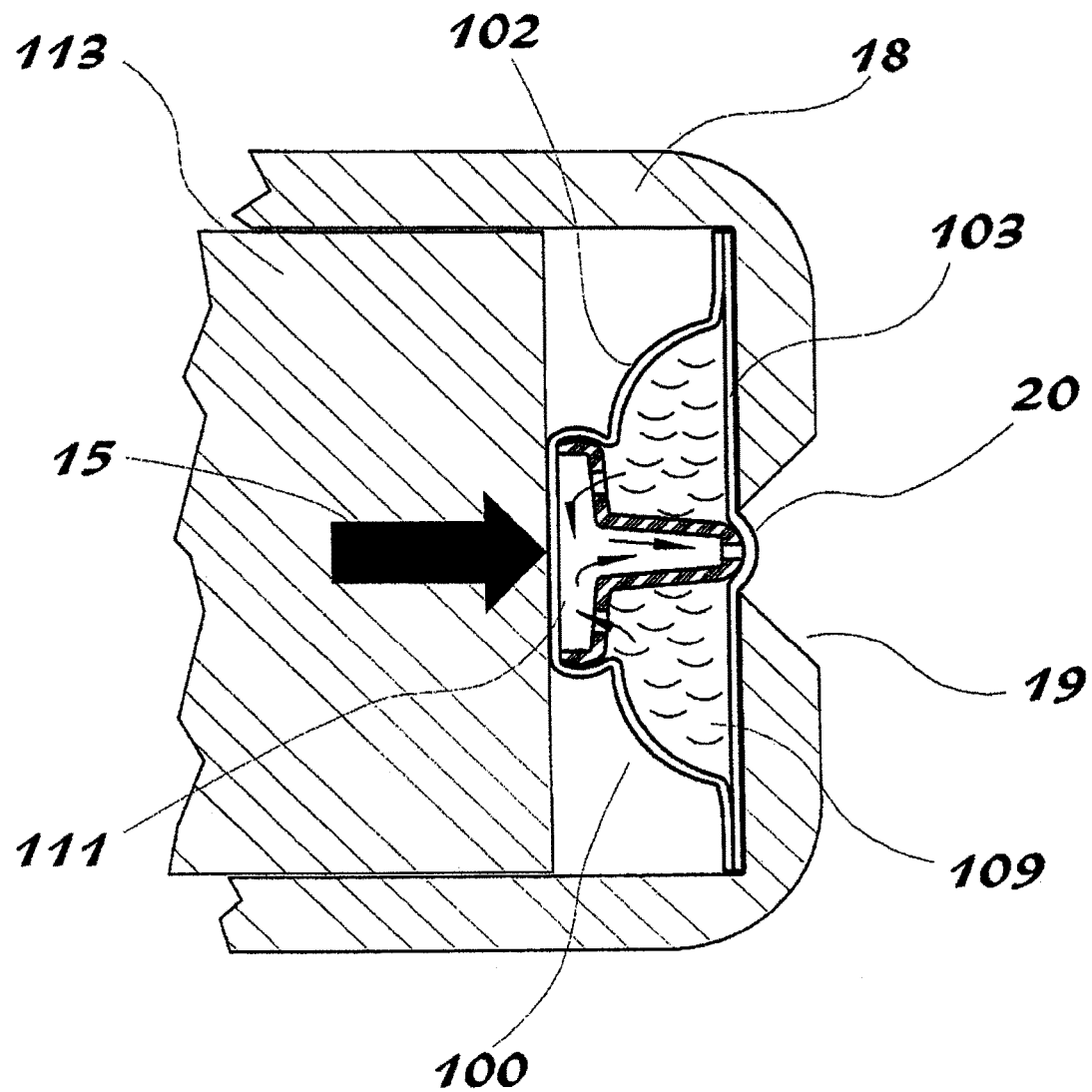
FIG. 6 is a view of the dosage form of FIG. 5 during an intermediate step of administration.
Figure 7:
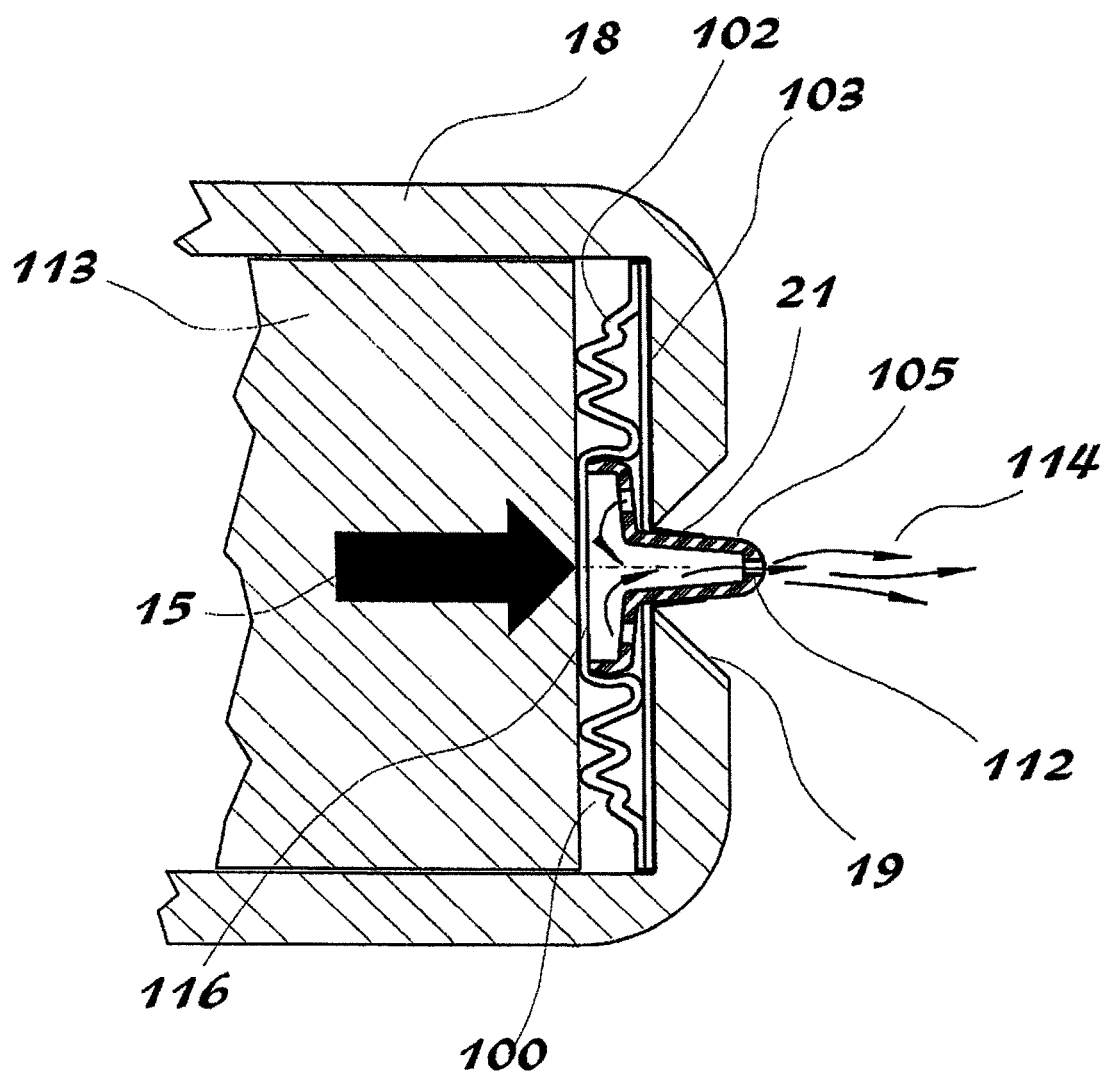
FIG. 7 is a view of the dosage form of FIG. 5 during discharge.

Blister dosage form 100 is shown in FIG. 5 positioned in a housing 18 with plunger 13 in the ready mode. Housing 18 has a discharge opening 19 to allow the piercing nozzle 105 to penetrate the membrane 103 during dispensing. As shown in FIG. 6, a force in direction 15 is applied to plunger 13 during the dispensing action, compressing the diaphragm 102 and driving the piercing nozzle 105 into the membrane 103 at piercing point 20. The next stage of dispensing is shown in FIG. 7. As the force continues to drive the plunger 13 against the diaphragm 102, the diaphragm collapses, driving piercing membrane 103 through the membrane and forcing the agent 109 through the piercing nozzle 105 and out the discharge port 112 in the discharge pattern 114. In this embodiment, the shape of the blister dosage form 100 is designed to conform to the plunger 13 and housing 18 of the dosing mechanism to insure that the diaphragm 102 seals to the piercing nozzle 105 in the contact area 116 and that the membrane 103 seals to the piercing nozzle 105 around the sealing area 21 in order to achieve the desired spray pattern 114.

Figure 8:
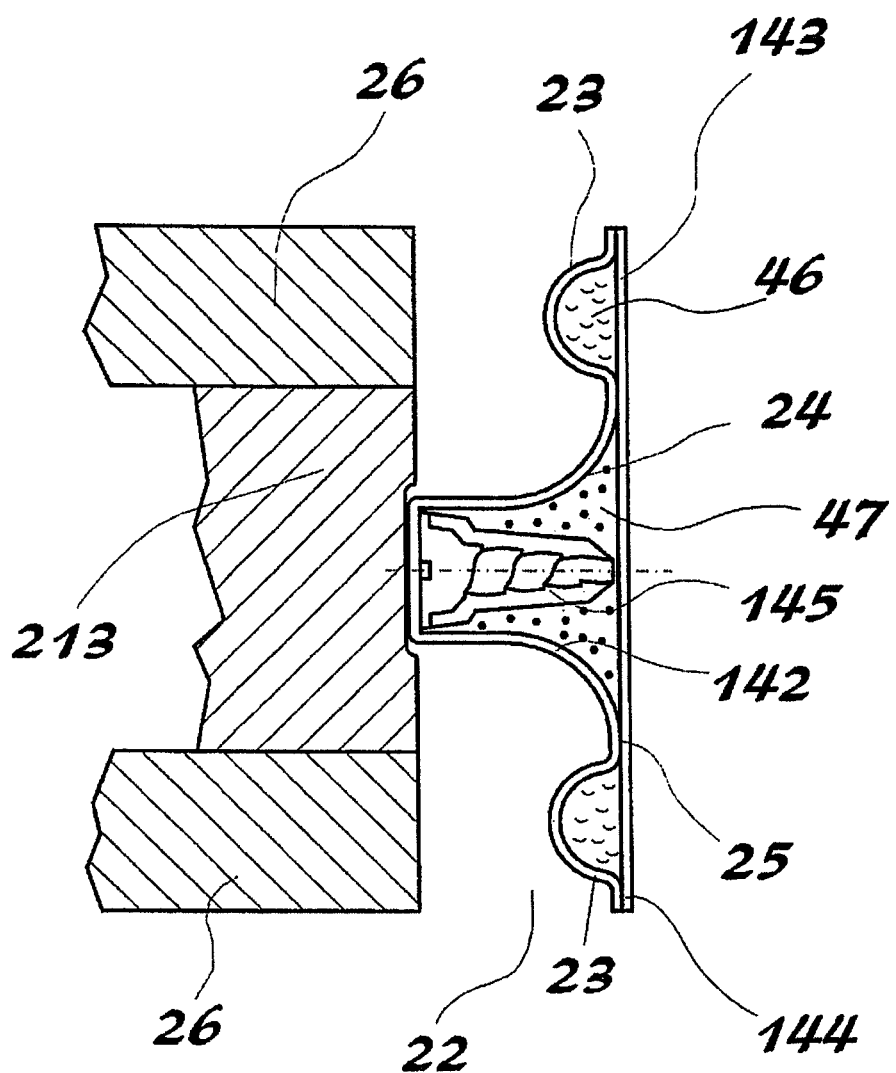
FIG. 8 is a cross section view of a dosage form with two dosage chambers and an internal piercing mechanism interacting with plungers of a delivery device.

In certain embodiments, the disclosure is directed to dosage forms that contain more than one pharmaceutical agent in separate chambers, or more than one component of a medication that is to be mixed or combined just prior to or during administration. The chambers may also have one pharmaceutical agent and a second component that is to be mixed or combined with the agent prior to administration. The pharmaceutical agents and mixing agents in separate chambers may be liquid compositions, solid compositions, or one or more liquid compositions and one or more solid compositions. The solid compositions may be, for example, powdered pharmaceutical compositions or lyophilized compositions. The pharmaceutical or mixing agents in the chambers are typically different, but the same pharmaceutical agent or mixing agent may be present in more than one chamber of the same dosage form. An example of a dual chambered blister dosage form 22 is shown in FIG. 8. This blister includes an outer ring shaped, or arcuate shaped chamber 23 filled with a first volume of agent 46 and an inner chamber 24 filed with a second volume of agent 47. Either agent 46 or 47 can be in powder form, but one of the two is preferably a liquid. The seal between the two chambers is a delamination zone 25. This area releases its seal between diaphragm 142 and membrane 143 at a lower pressure than the bursting strength of the diaphragm material and at lower pressure than the seal area 144. This concept also utilizes an outer plunger 26, which is also essentially a round member and can move independently of the plunger 13.

Figure 9:
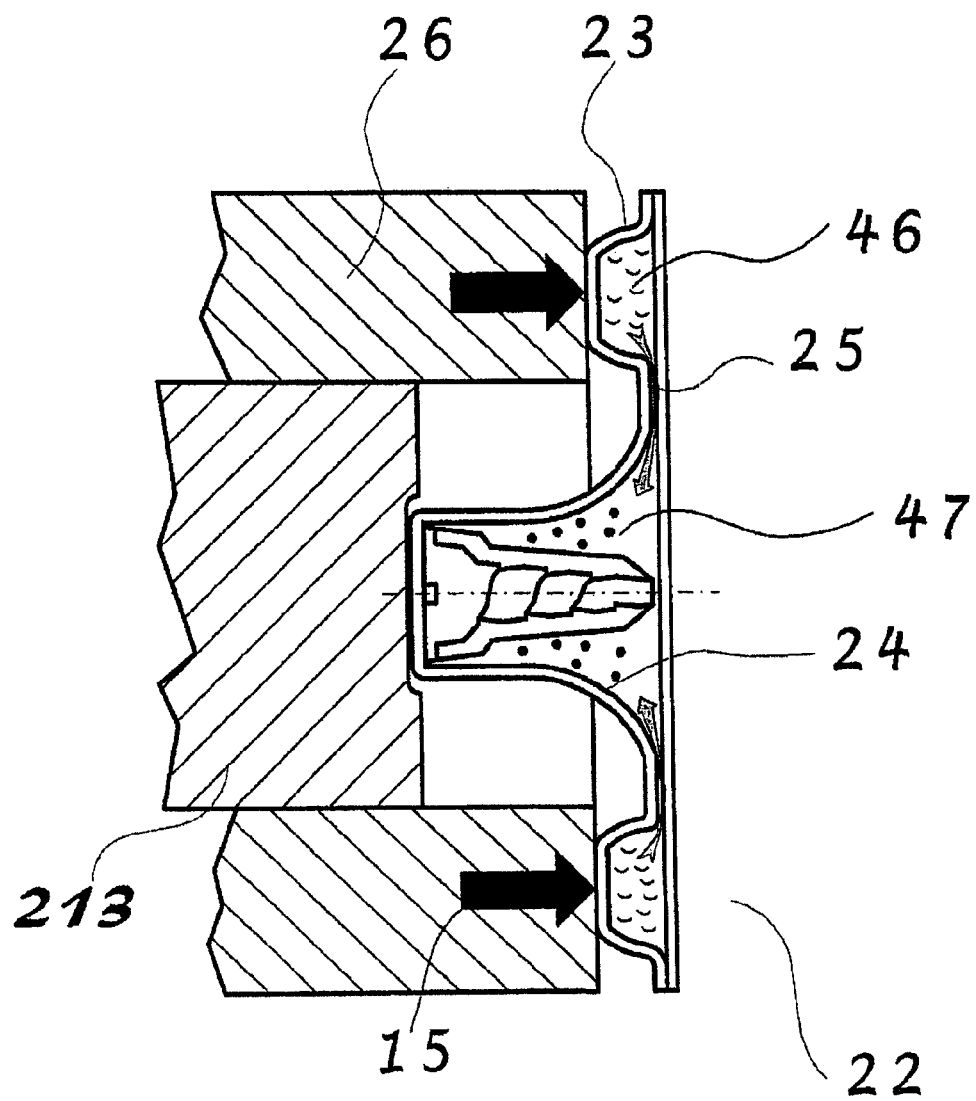
FIG. 9 is a cross section view of the dosage form of FIG. 8 in the first step of administration.
Figure 10:
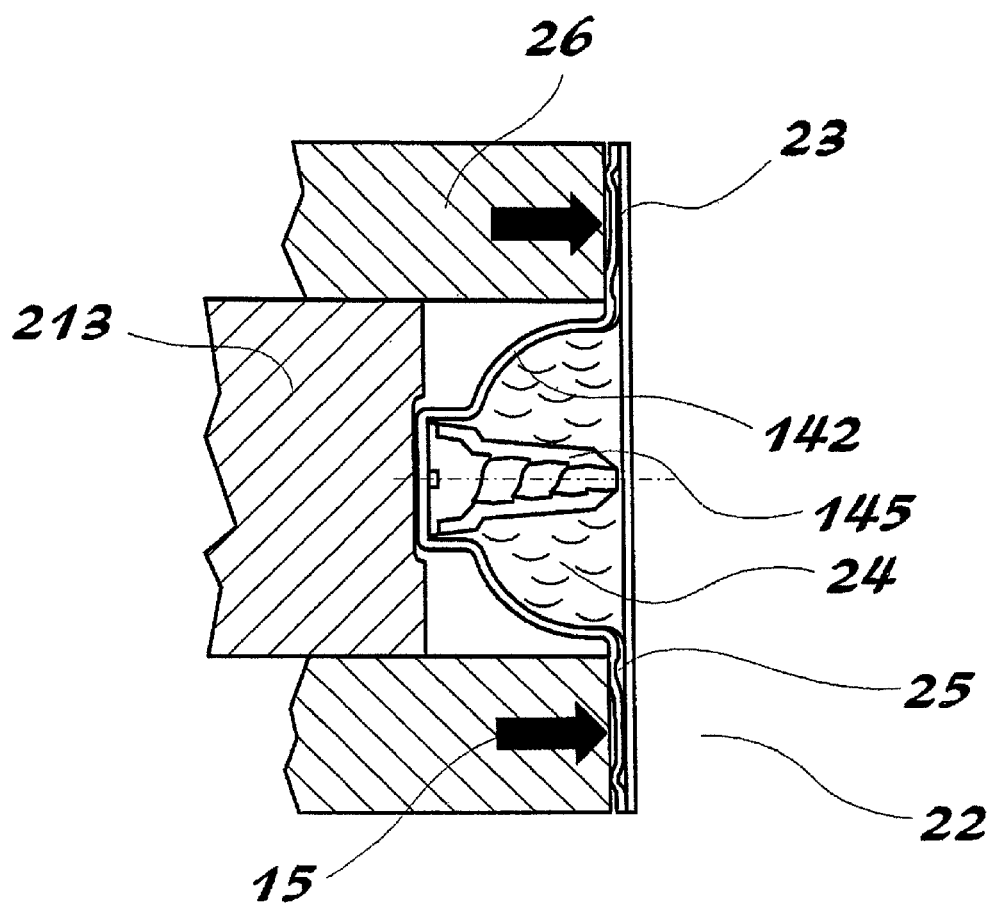
FIG. 10 is a cross section view of the dosage form of FIG. 8 in an intermediate step of administration.
Figure 11:
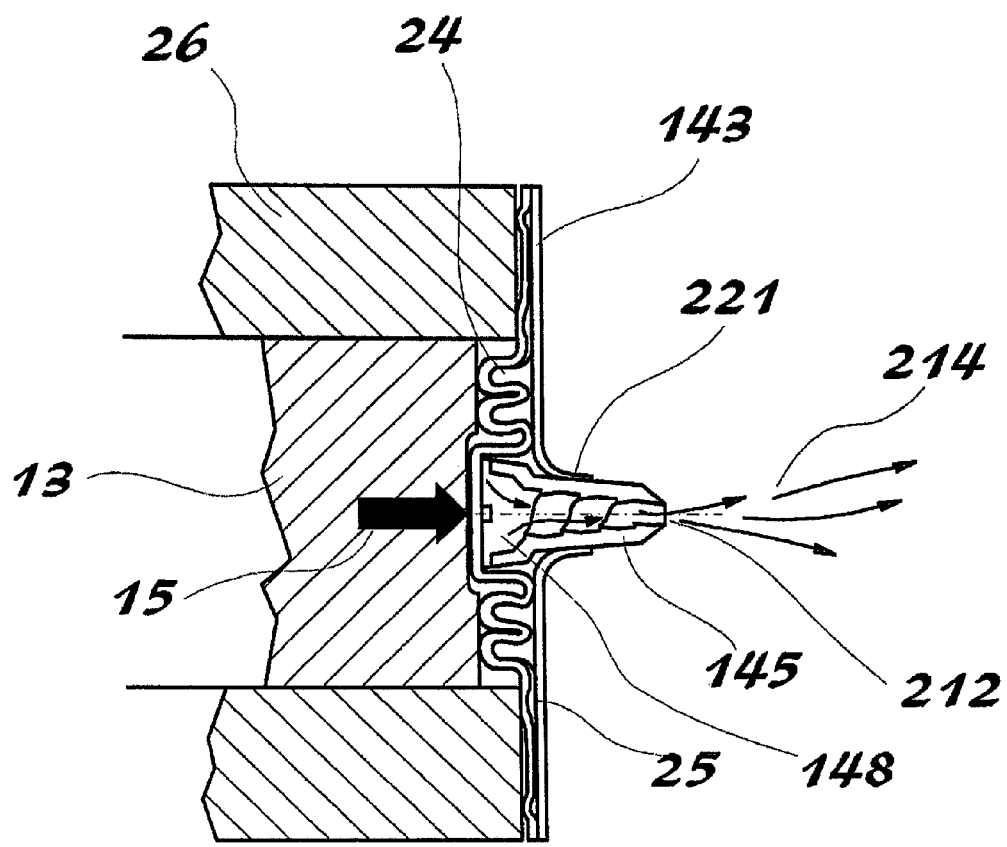
FIG. 11 is a cross section view of the dosage form of FIG. 8 during discharge.

The dosage form 22 is shown during the dispensing steps in FIGS. 9, 10 and 11. In the first stage, the outer plunger 26 is forced against the outer chamber 23. As the critical pressure is reached, the delamination zone 25 releases its seal and the first agent 46 is driven into the inner chamber 24 and mixes with the second agent 47. As the outer plunger 26 is completely depressed as shown in FIG. 10, and the outer chamber 23 is completely collapsed, all the first agent 46 is forced into the inner chamber 24, causing the diaphragm of the inner chamber 24 to expand to a domed shape containing the contents of both chambers. A comparison of FIGS. 9 and 10 illustrates this expansion, as the sides of the inner chamber are concave (in the two dimensional drawing) in FIG. 9 and expand to a convex shape in FIG. 10. The final stage is demonstrated in FIG. 11, where the force is applied to the inner plunger 13 so that it presses the piercing nozzle 145 through the membrane 143 and collapses the inner chamber 24, expelling the mixture of first agent 46 and second agent 47 through the inner chamber 148 and out the discharge port 212 in the desired discharge pattern 214. The seal between contact area 116 and the sealing area 221 again force all the agents to pass through the piercing nozzle 145, resulting in the desired spray configuration.

Figure 12:
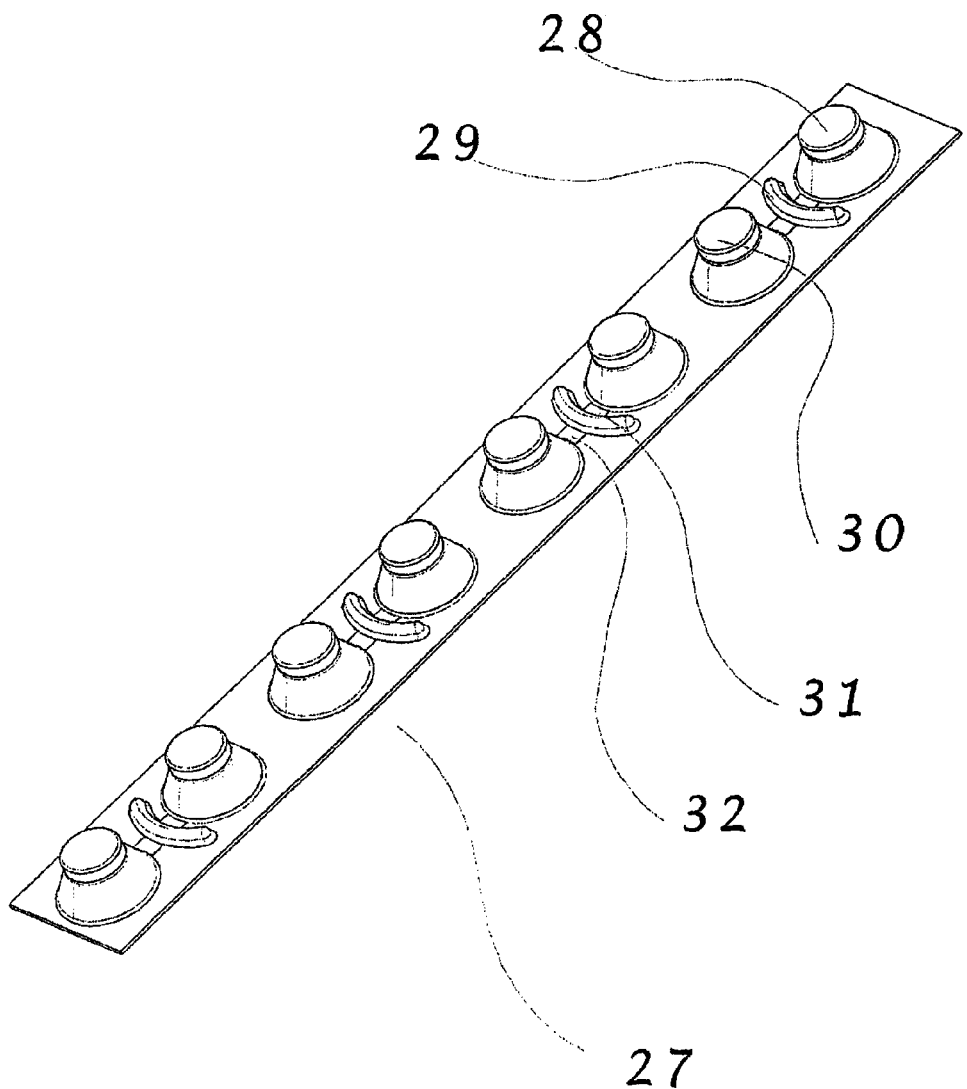
FIG. 12 is an embodiment of a dual chambered dosage form on a strip for sequential administration of multiple dosages.
Figure 13:
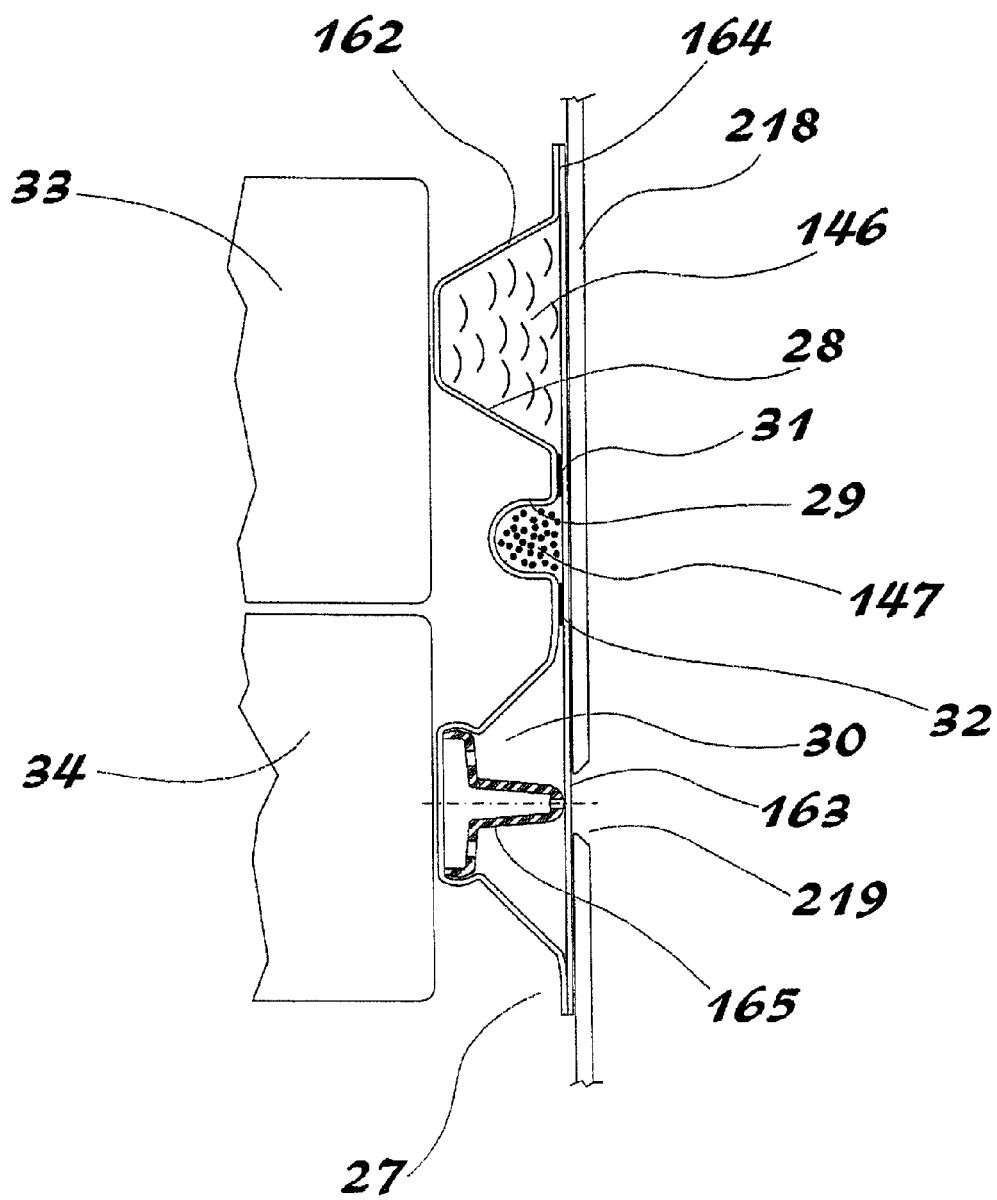
FIG. 13 is a cross section view of an embodiment of a dual chambered dosage interacting with pistons of a delivery device.
Figure 14:
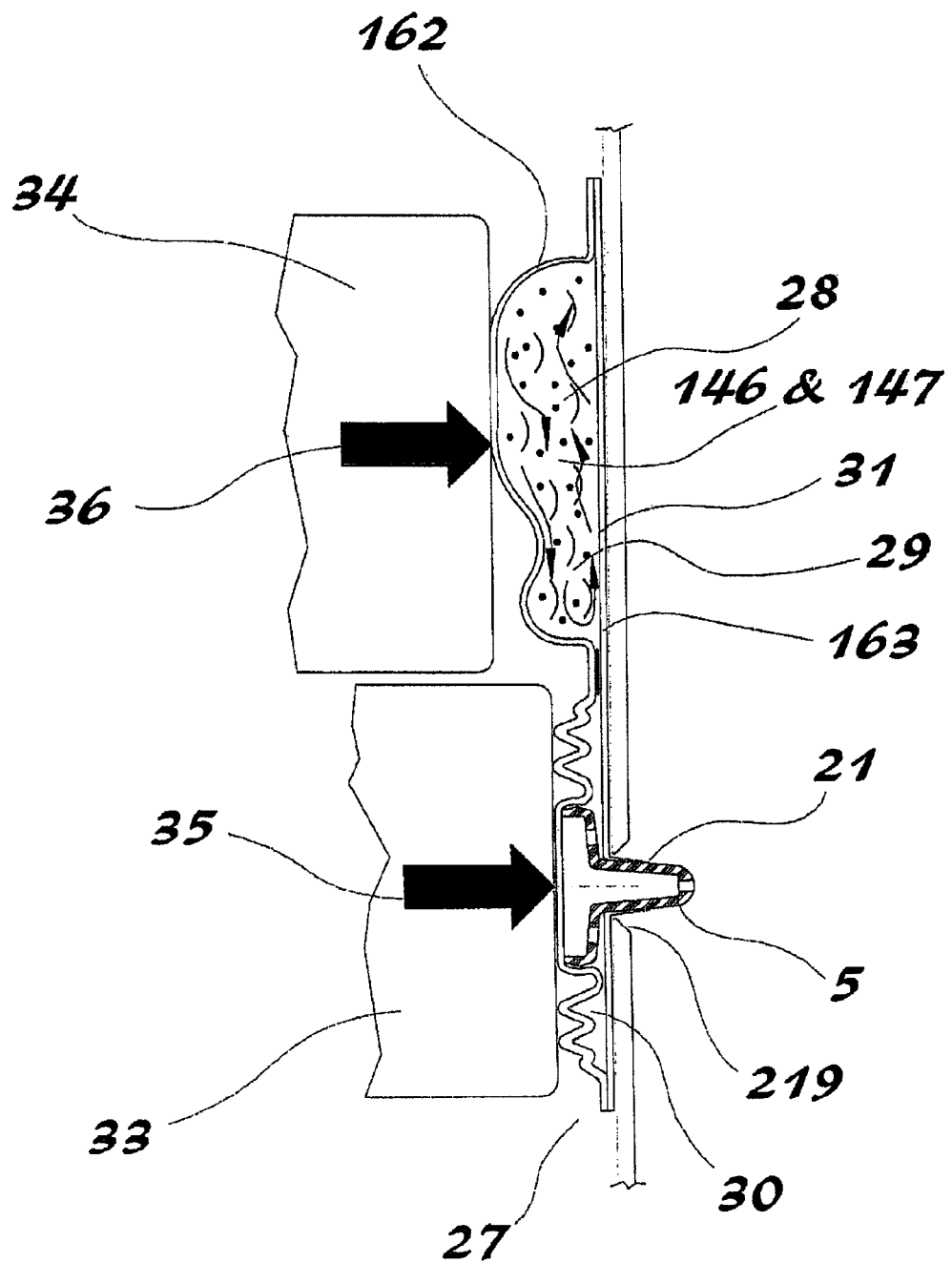
FIG. 14 is a cross section view the dosage form of FIG. 13 during the first stage of administration.
Figure 15:
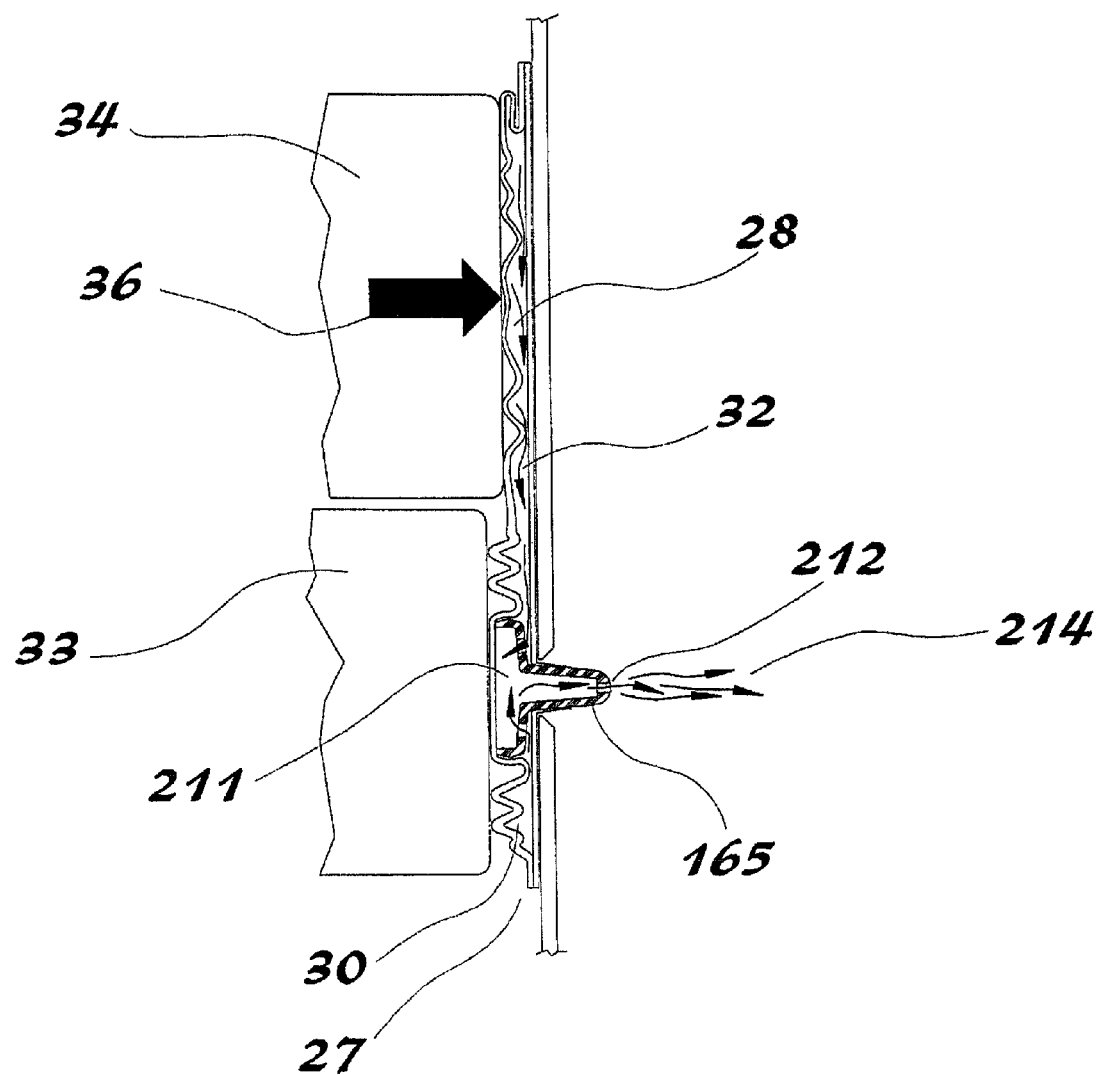
FIG. 15 is a cross section view the dosage form of FIG. 13 during discharge.

In certain embodiments, a dosage form that contains two separated components can be manufactured on a dosage strip 27 as shown in FIG. 12. The strip can be used in an appropriate dispensing device to deliver repeated doses of the pharmaceutical agent or mixture comprising one or more pharmaceutical agents. Each unit of the strip includes a first dosage chamber 28 connected to a second dosage chamber 29 by a first delamination zone 31 and a dispensing chamber 30 connected to the second dosage chamber 29 by a second delamination zone 32. A unit of the dosage strip 27 is shown in FIG. 13 as if positioned in a housing 218 with first plunger 33 which operates independently of second plunger 34. First chamber 28 contains a first component 146 of a pharmaceutical dose, and second chamber 29 contains a second component 147. The housing 18 includes a discharge opening 219 positioned in front of piercing nozzle 165. In the first stage of dispensing the combined agent(s) as shown in FIG. 14, a first force 35 pushes the first plunger 33, collapsing the dispensing chamber 30, and driving the piercing nozzle 165 through the membrane 163. A second force 36 then pushes the second plunger 34 against the first dosage chamber 28, causing the first delamination zone 31 to release its seal and causing the first component 146 to mix with the second component 147. As shown in FIG. 15, when the second plunger 34 is completely depressed, it causes the collapse of the combined chambers and drives the agent mixture through the dispensing chamber 30, through the piercing nozzle 165 and out discharge port 212 in discharge pattern 214.

Figure 16:
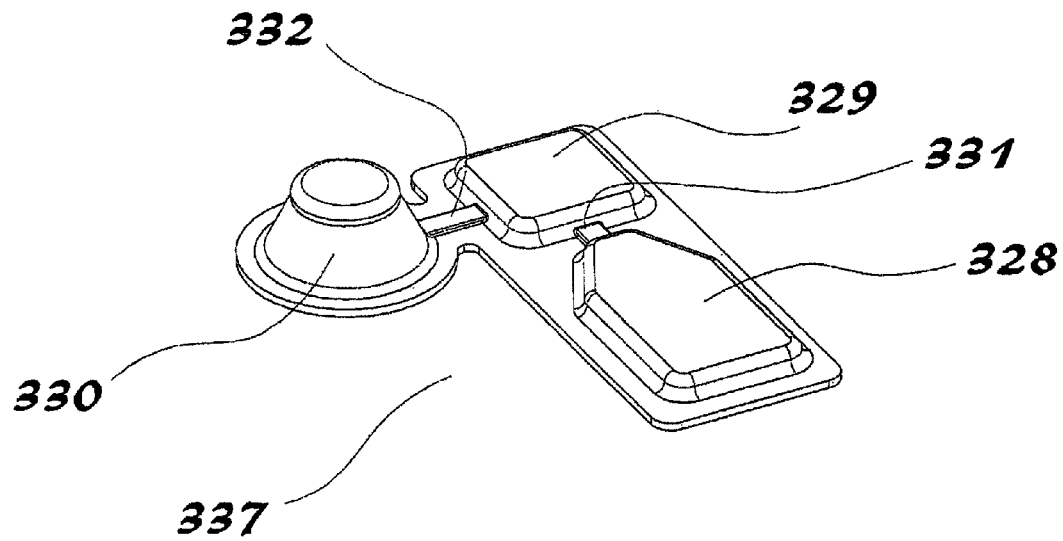
FIG. 16 is a perspective view of a dosage form as manufactured.
Figure 17:
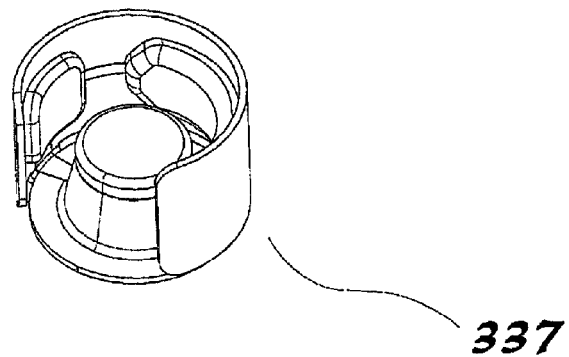
FIG. 17 is a perspective view of the dosage form of FIG. 16 formed into a cylindrical shape for use in a delivery device.
Figure 18:
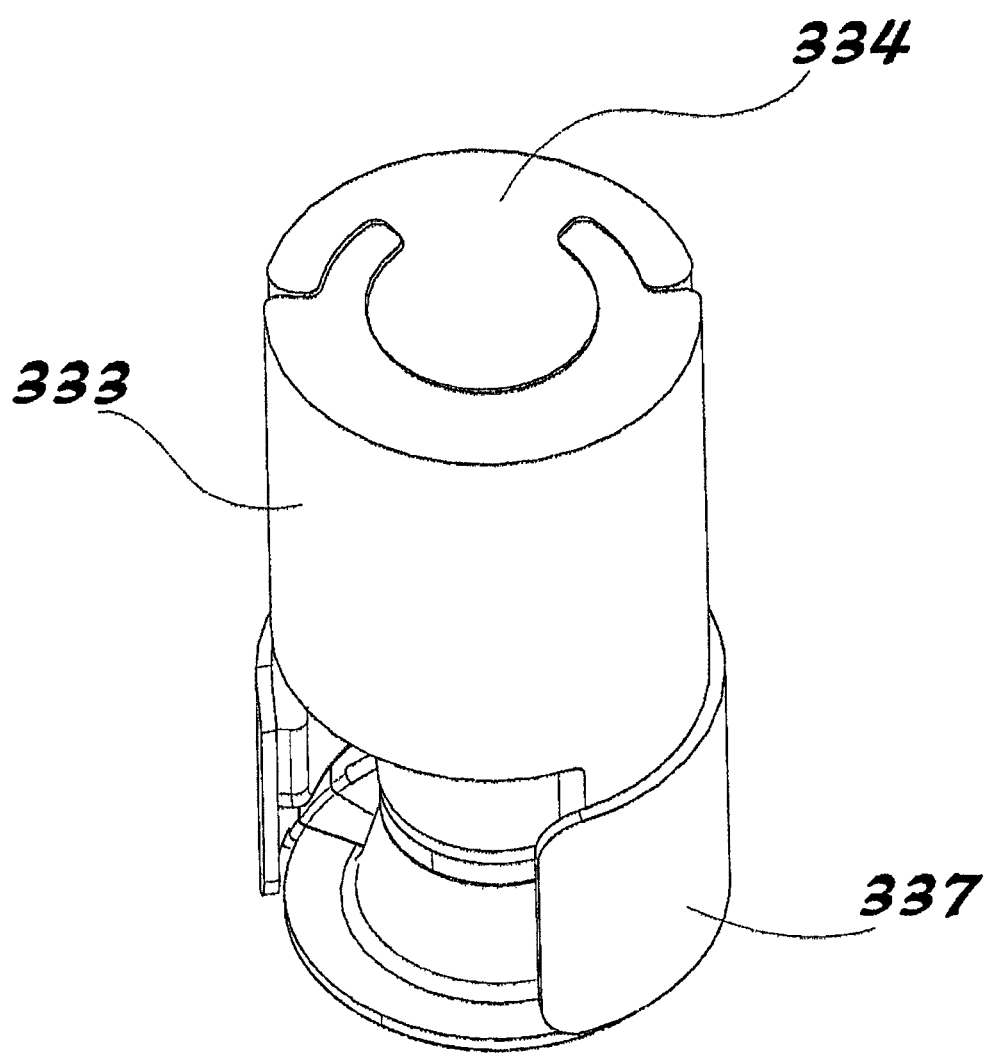
FIG. 18 is a perspective view of the dosage form of FIG. 16 in the housing of a delivery device.
Figure 19:
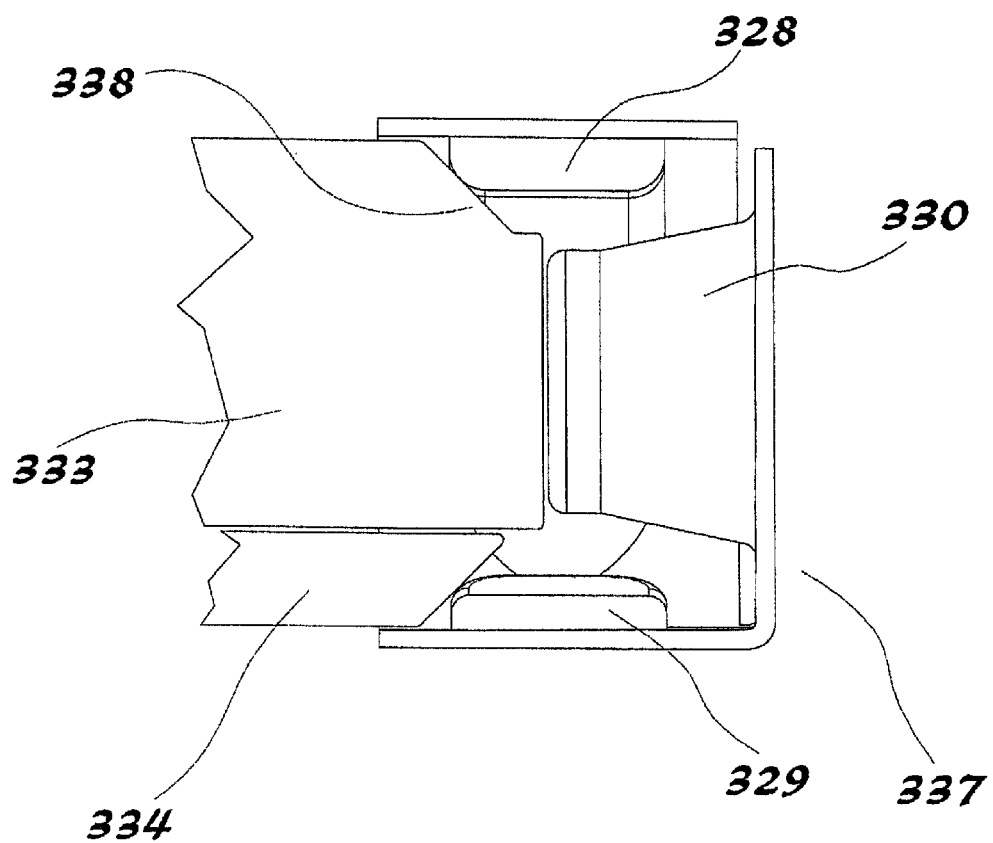
FIG. 19 is a cross section view of the dosage form of FIG. 16 in a housing of a delivery device in the ready mode.
Figure 20:
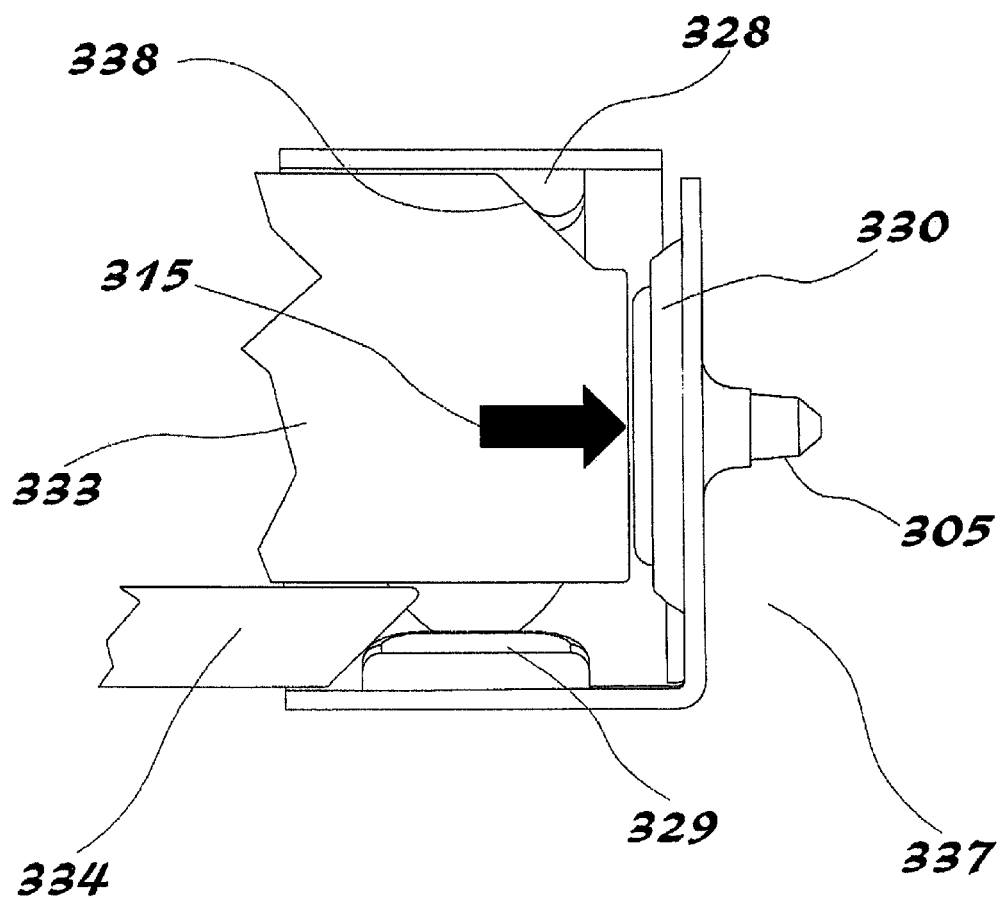
FIG. 20 is a cross section view of the dosage form of FIG. 16 in the first step of administration.
Figure 21:
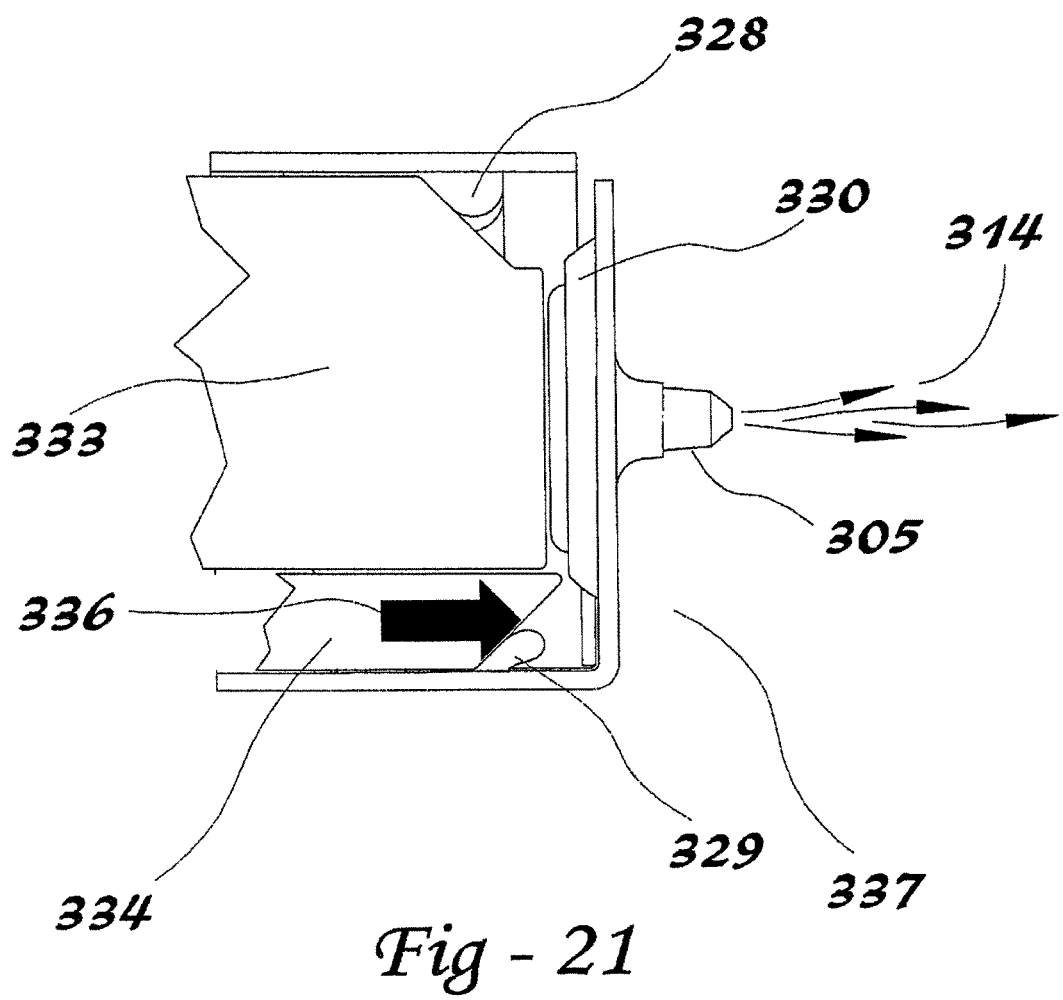
FIG. 21 is a cross section view of the dosage form of FIG. 16 during discharge.

An alternative dual chamber blister dosage form 337 is shown in FIG. 17. The dosage form 337 includes a first dosage chamber 328, a first delamination zone 331, a second dosage chamber 329, a second delamination zone 332 and a dispensing chamber 330. The blister can be manufactured as a flat piece as shown in FIG. 16, and folded into a circular shape as shown in FIG. 17 to for use with a cylindrical housing for dispensing. FIG. 18 shows a portion of a dispensing device that has two independently operated plungers 333, 334 adjacent the dosage form. As shown in FIG. 19 the first plunger 333 contains a sloped cam surface 338 and is positioned against the dispensing chamber 330 and the first dosage chamber 328. When sufficient force 315 is applied to the first plunger 333, as shown in FIG. 20, the plunger collapses the dispensing chamber 330, and drives the piercing nozzle 305 through the membrane 303 and, simultaneously, forces the collapse of a portion of first dosage chamber 328 separating first delamination zone 331 and mixing the agents. When the second plunger 334 is fired, as shown in FIG. 21, it causes the collapse of the remaining portion of the first dosage chamber 328 and also crushes the second dosage chamber 329, releasing the second delamination zone 332, and driving the mixed components out of piercing nozzle 305 in discharge pattern 314.

Figure 22:
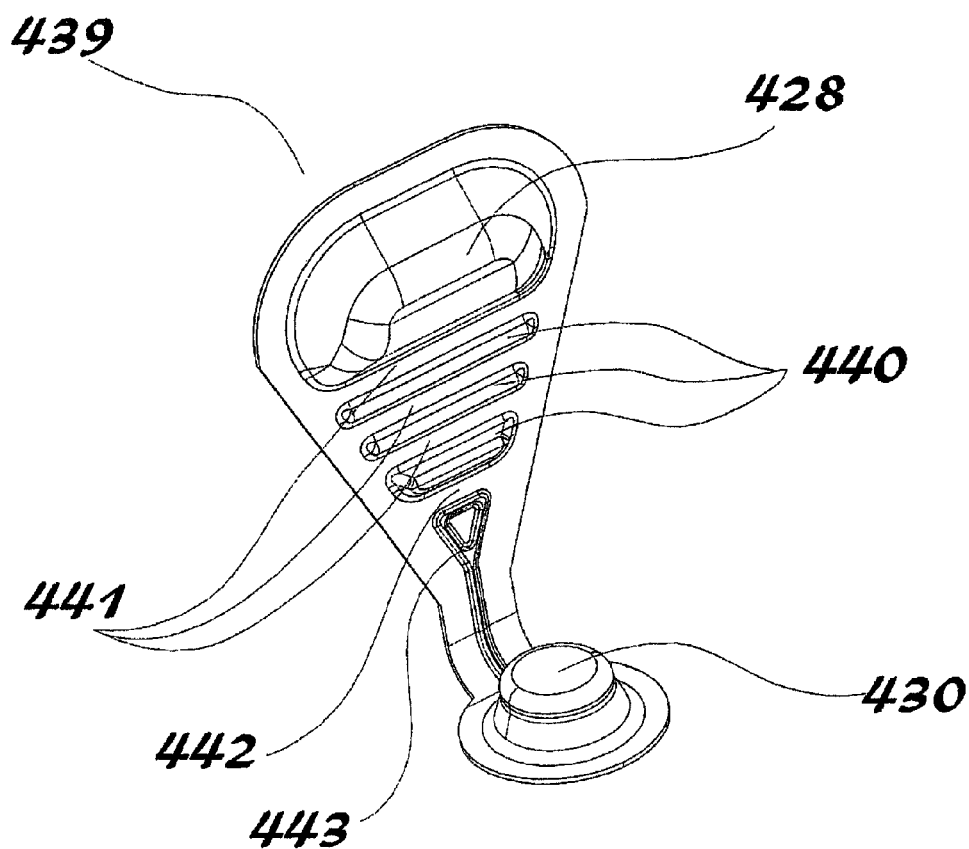
FIG. 22 is a perspective view of a dosage form with multiple dosage chambers.
Figure 23:
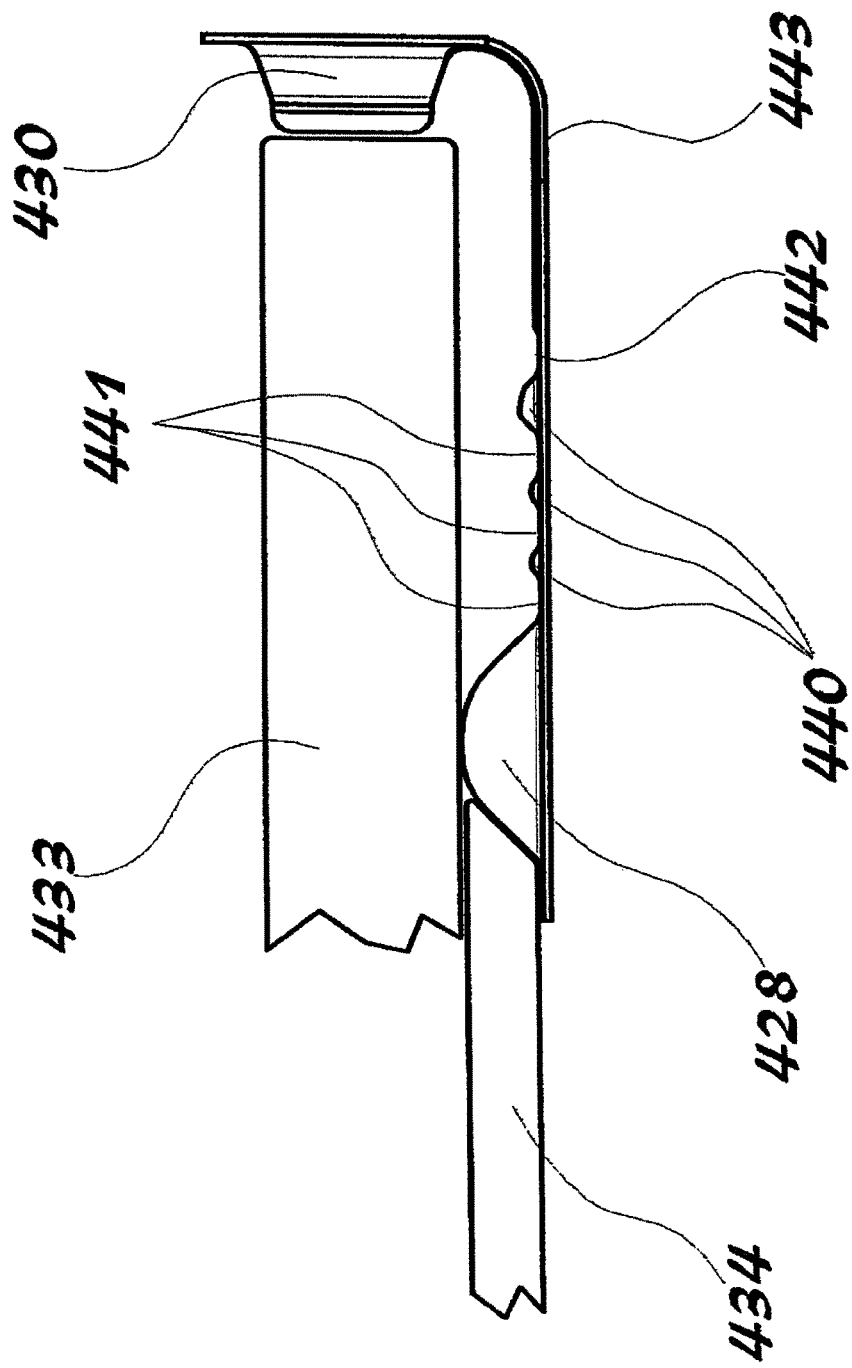
FIG. 23 is a cross section view of the dosage form of FIG. 22 in a housing of a delivery device in the ready mode.
Figure 24:
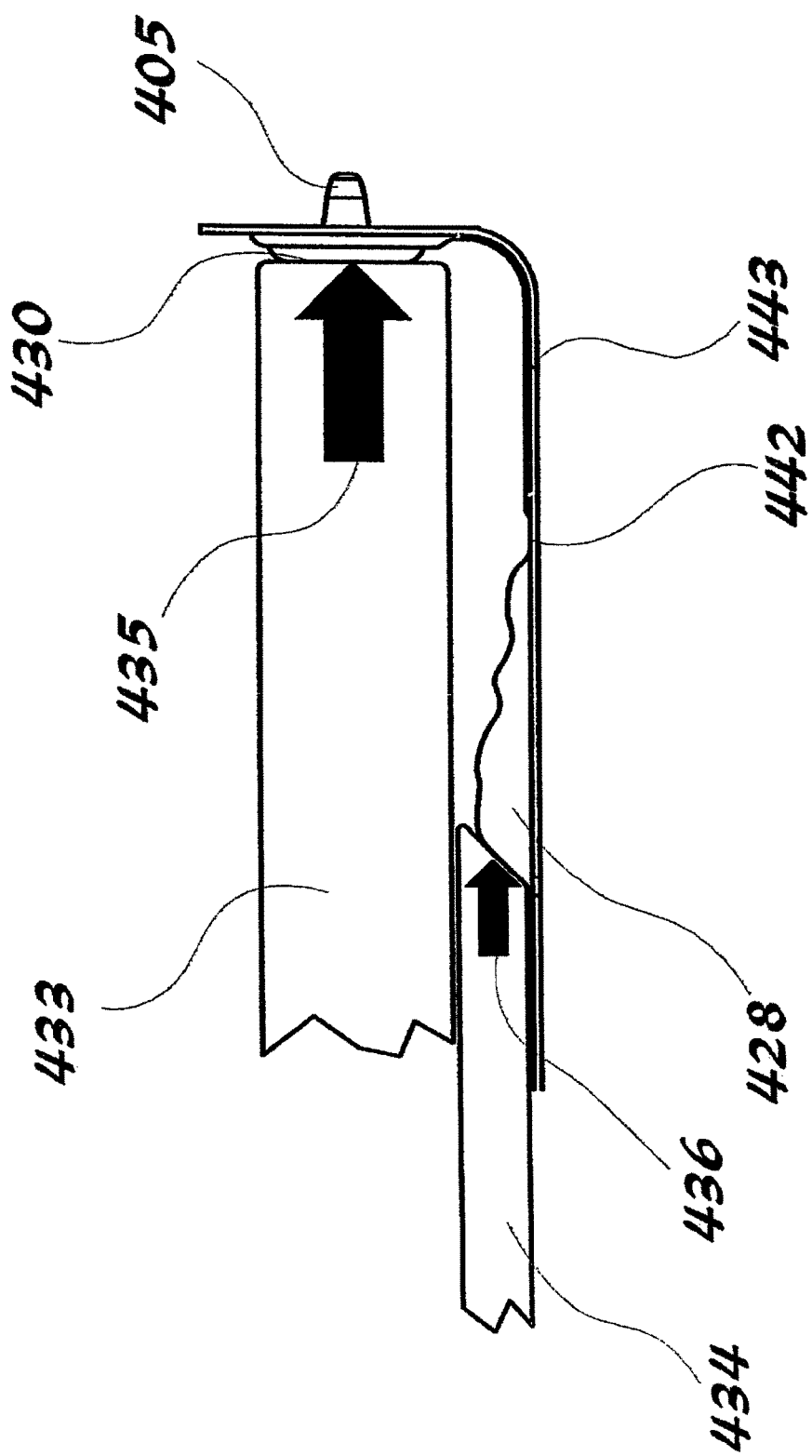
FIG. 24 is a cross section view of the dosage form of FIG. 22 in the first step of administration.
Figure 25:
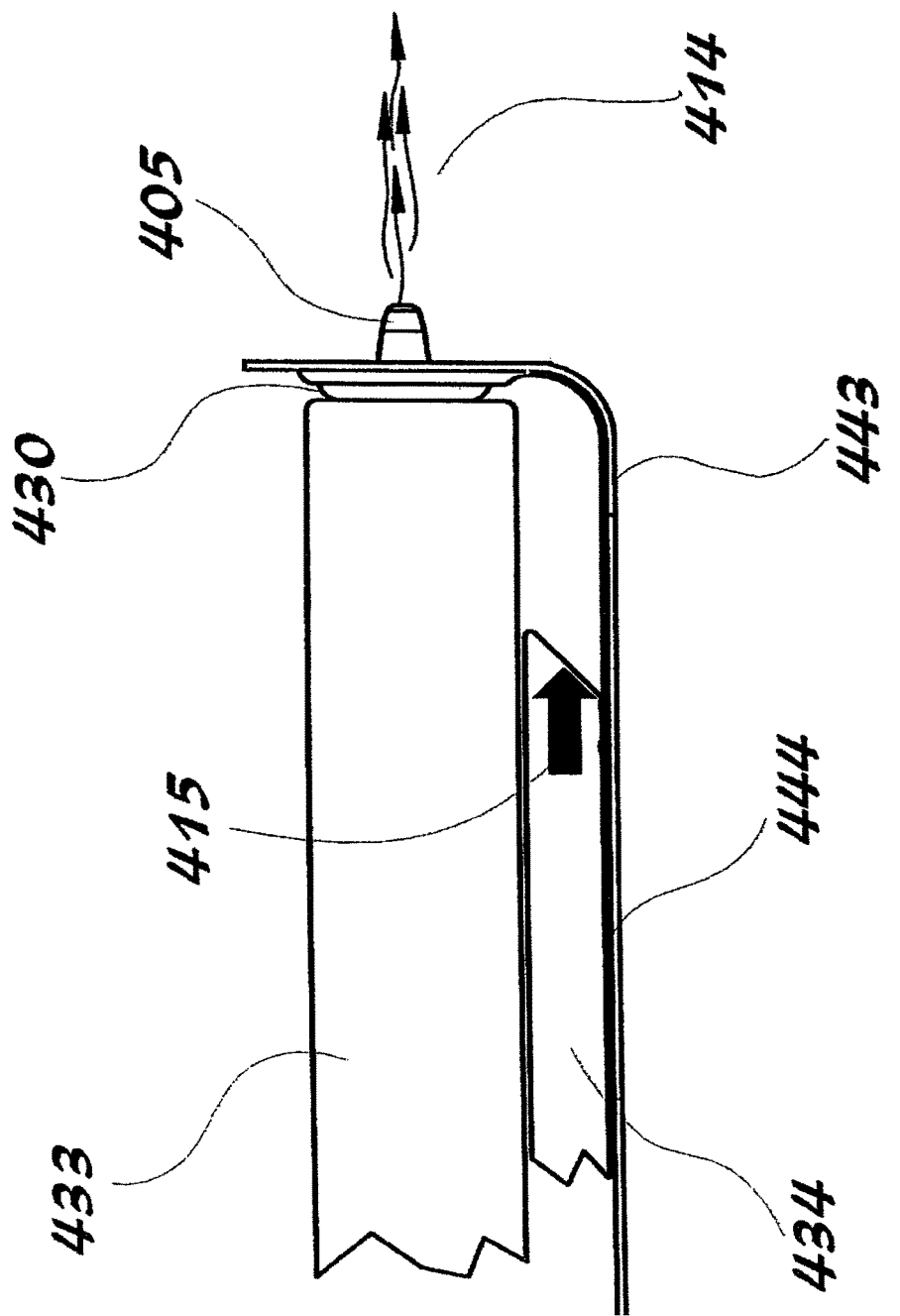
FIG. 25 is a cross section view of the dosage form of FIG. 22 during discharge.
Figure 26:
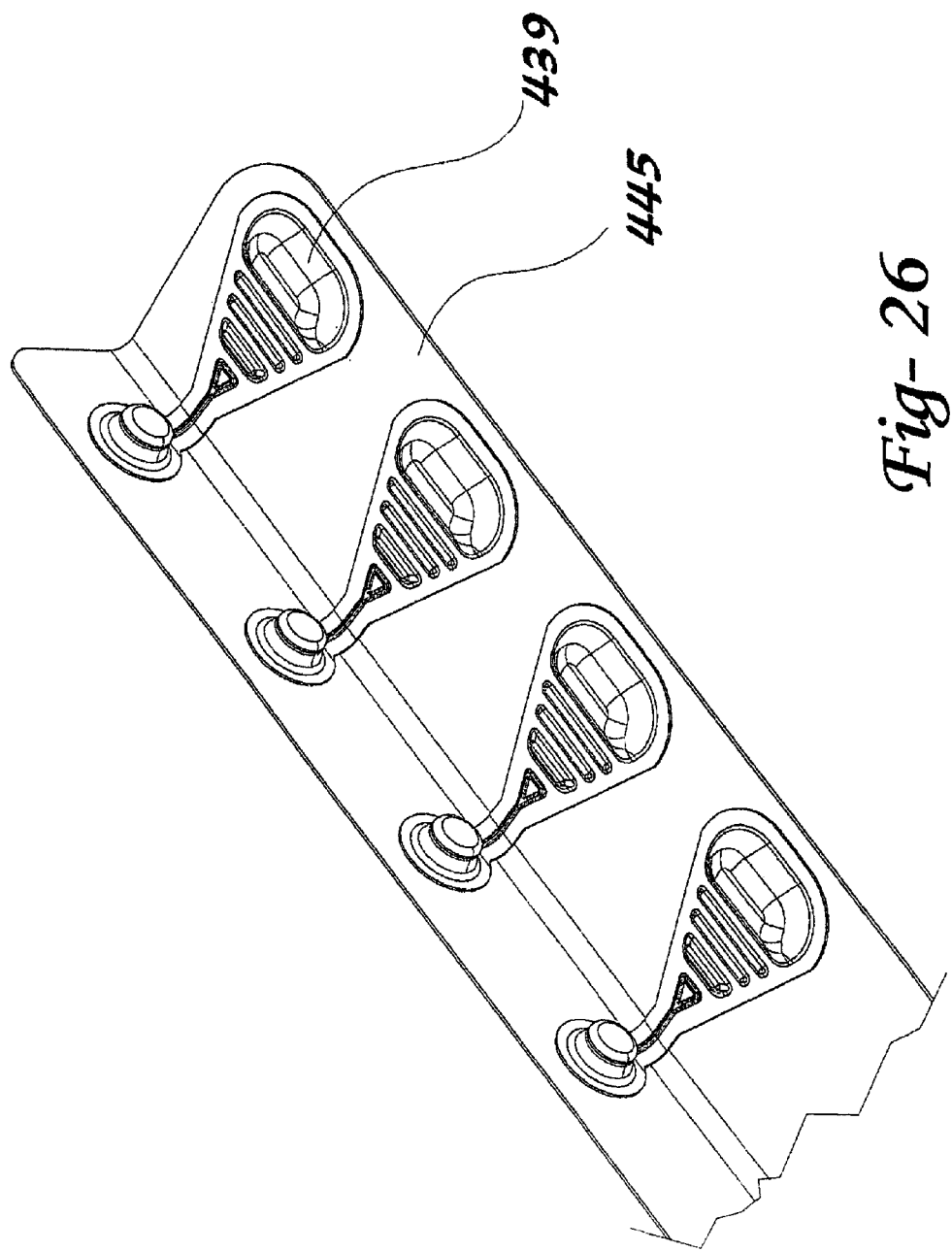
FIG. 26 is a perspective view of the dosage form of FIG. 22 on a strip for sequential administration of multiple dosages.

An embodiment of a multi-chambered dosage form 439 is shown in FIG. 22. This embodiment can be used for medications that have more than two agent components to mix into a single dose. The dosage form in FIG. 22, for example can be used to mix four separate components. Between the four component chambers 428 and 440 are three initial delamination zones 441. A final delamination zone 442 connects to a discharge channel 443 which in turn, connects to the dispensing chamber 430. The dosage form 439 is designed for use in a housing with independently separately operated plungers, 433 and 434 as shown in FIG. 23. When the agent is to be dispensed as shown in FIG. 24, the first plunger 433 collapses the dispensing chamber 430. The second plunger 434 is driven into the first dosage chamber 428, releasing the seal of the initial delamination zones 441 and mixing the components in the resulting expanded chamber containing all the components. As the second plunger 434 continues to further collapse the mixed chamber, (FIG. 25) the final delamination zone 442 releases, and the mixed components flow through the discharge channel 443, through the piercing nozzle 405 and are discharged in the desired pattern 414. FIG. 26 is an illustration of multiple angle blister dosage forms 439 mounted on an angled strip 445 to enable multiple deliveries of the mixed components.

Figure 27:
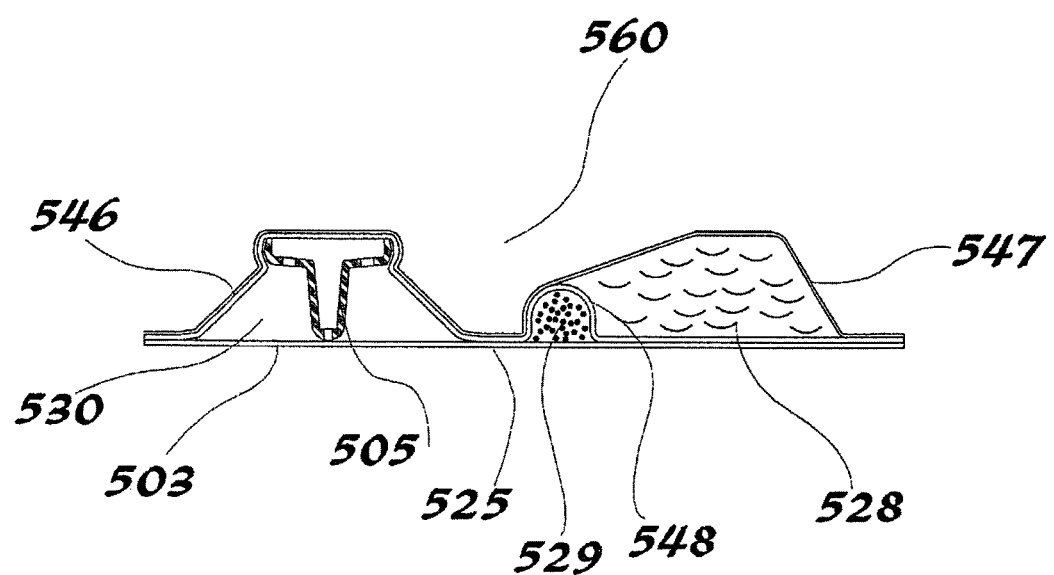
FIG. 27 is a cross section view of an embodiment of a dual chambered dosage form in which the dosage components are separated by a high vapor barrier material.

Certain embodiments of the disclosure are designed to seal a pharmaceutical agent in a blister chamber that has very low permeability to prevent water vapor from reaching the agent. An example of such an embodiment is shown in FIG. 27. The dual chambered blister dosage form 560 utilizes a tri-layer film 546 to form the membrane and the diaphragm. The middle layer 548 and membrane layer 503 are made of high vapor barrier materials such as aluminum foil. The top layer 547 is made from flexible diaphragm material. The first dosage chamber 528 is formed between the top layer 547 and the middle layer 548. The second dosage chamber 529 is formed between the middle layer 548 and the membrane 503 such that the agent in the second dosage chamber 529 is hermetically sealed from the liquid agent in the first dosage chamber 528. The second dosage chamber 529 is separated from the dispensing chamber 530 by a delamination zone 525.

Figure 28:
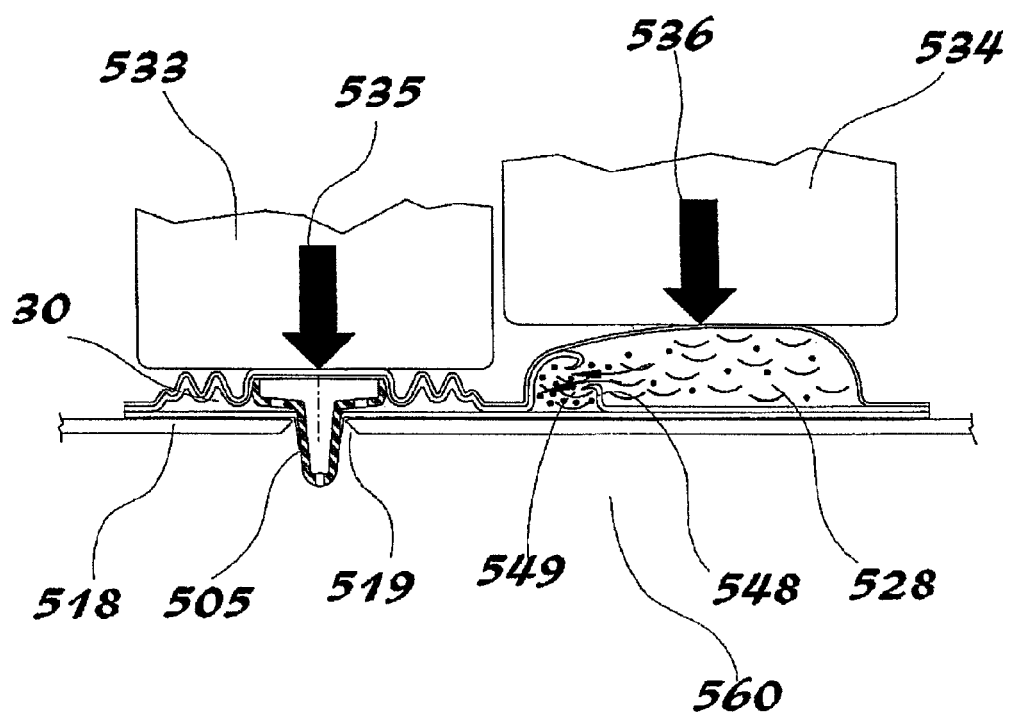
FIG. 28 is a cross section view of the dosage form of FIG. 27 in the first step of administration.
Figure 29:
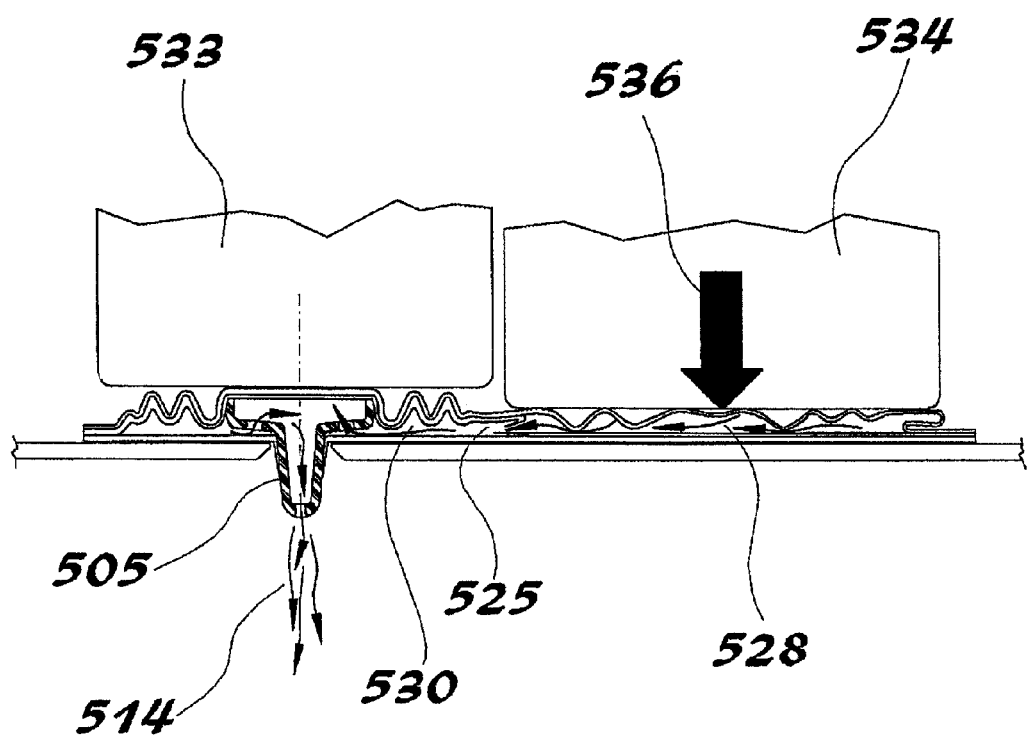
FIG. 29 is a cross section view of the dosage form of FIG. 27 during discharge.

In the initial step of dispensing the components as shown in FIG. 28 a first force 535 is applied to the first plunger 533 collapsing the dispensing chamber 530 and driving the piercing nozzle 505 through the discharge opening 519 in the housing 518. A second force 536 is applied to the second plunger 534 causing first dosage chamber 528 to compress and produce a break 549 in the middle layer 548 between the first dosage chamber 528 and the second dosage chamber 529 and allowing the components to mix. Break 549 can be focused at a desirable location by thinning the middle layer 548 at the desired location or by weakening the middle layer 548 by scribing, making a partial laser cut, or other means. As the second plunger 534 continues to travel, the first dosage chamber 528 is completely collapsed, forcing the delamination zone 525 to open and allowing the mixed components to flow through the dispensing chamber 530 and out the piercing nozzle 505 in discharge pattern 514.

Figure 30:
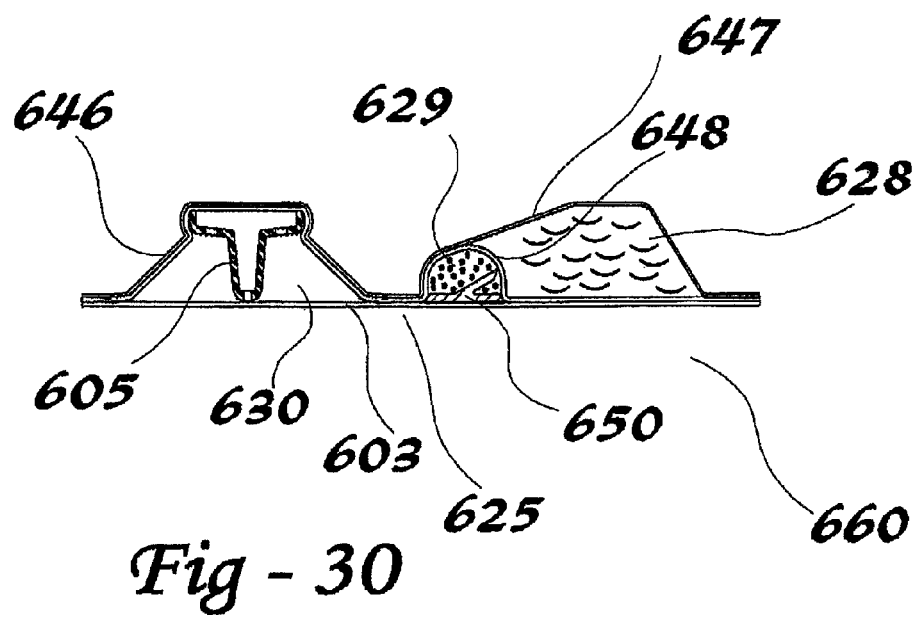
FIG. 30 is a cross section view of an embodiment of a dual chambered dosage form in which the dosage components are separated by a high vapor barrier material, and in which one of the chambers includes a piercing device.
Figure 31:
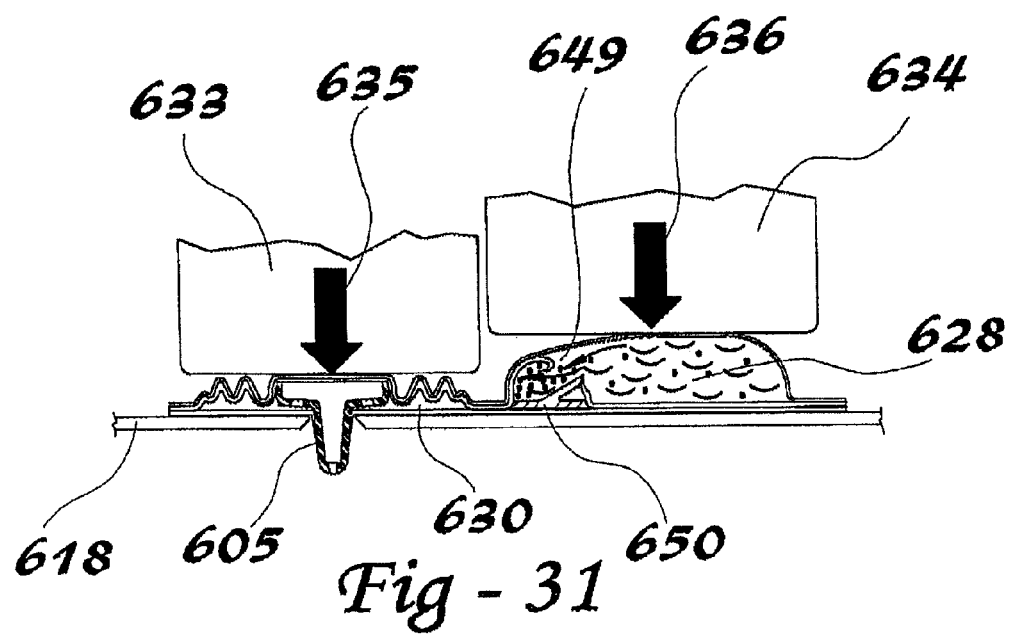
FIG. 31 is a cross section view of the dosage form of FIG. 30 in the mixing stage of administration.

Another embodiment of a blister dosage form with a tri-layer film is shown in FIG. 30. This embodiment 660 utilizes a tri-layer film 646 with a first dosage chamber 628, a second dosage chamber 629, a delamination zone 625 and a dispensing chamber 630, and an internal piercing member 650 inside the second dosage chamber 629. The piercing member can be located in the first dosage chamber 628 in other embodiments. During use, (FIG. 31) a first force 635 is applied to first plunger 633 collapsing the dispensing chamber 630 and a second force 636 is applied to the second plunger 634 compressing the first dosage chamber 628. The pressure in the first dosage chamber 628 presses the middle layer 648 against the point of the piercing member 650 causing a break 649 in the middle layer 648 and allowing the agents to mix. Continued travel of the second plunger 634 causes the complete collapse of the first dosage chamber 628, separation of the delamination zone 625, and discharge of the mixed components.

Figure 32:
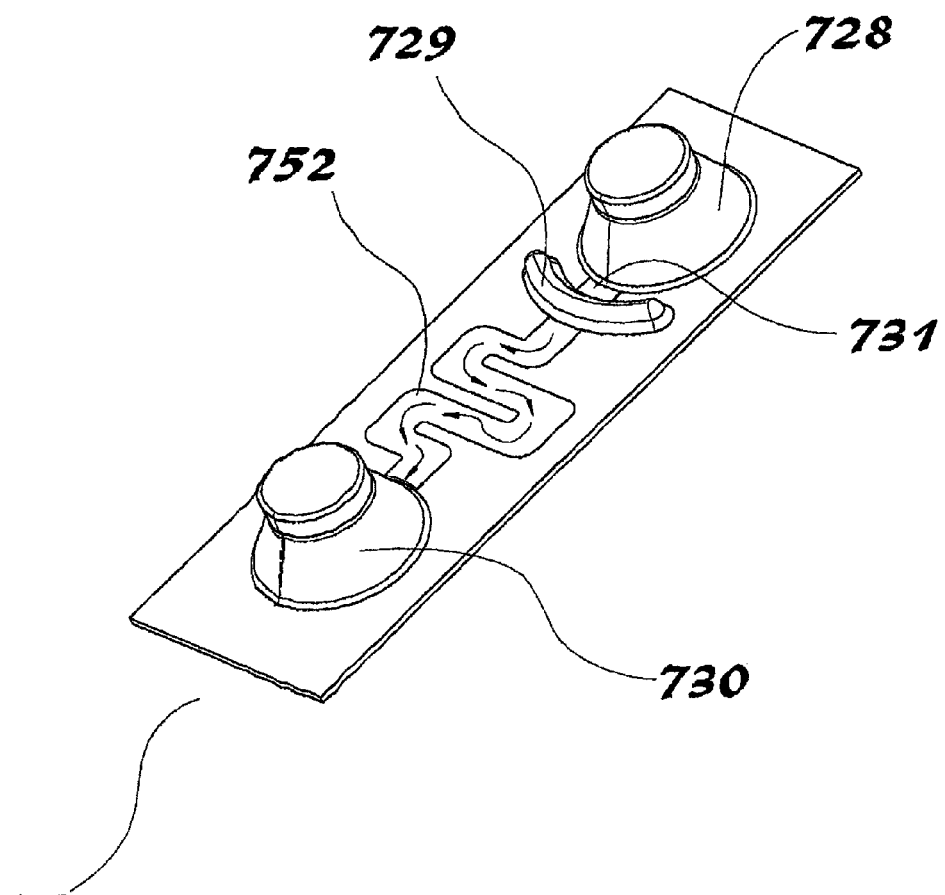
FIG. 32 is a perspective view of an embodiment of a dosage form in which the final delamination zone provides structure to promote mixing of the contents of the dosage chambers during administration.
Figure 35:
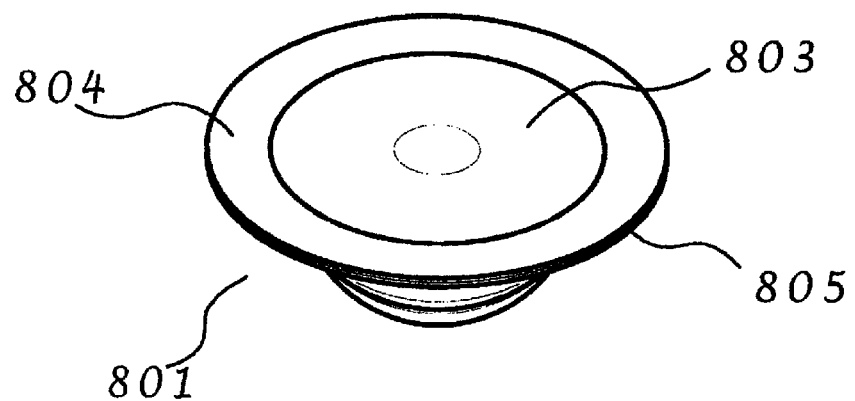
FIG. 35 is a perspective view of a trimmed dosage form.
Figure 36:
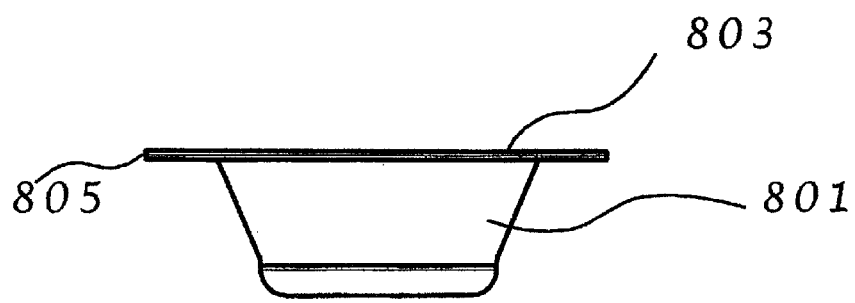
FIG. 36 is a side view of the dosage form shown in FIG. 35.
Figure 37:
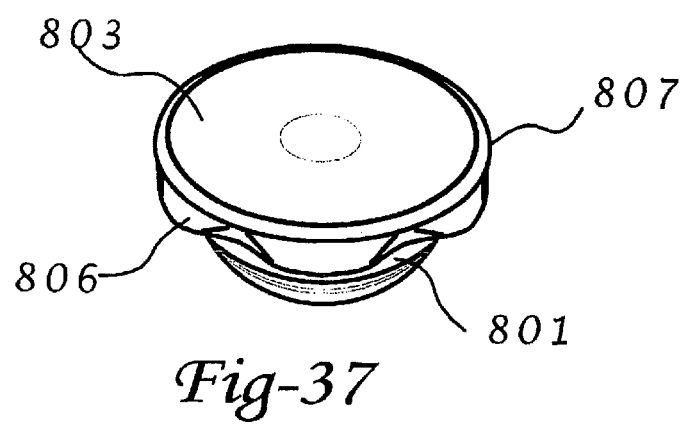
FIG. 37 is a view of the dosage form after swaging the rim to reduce the outside diameter of the dosage form.
Figure 38:
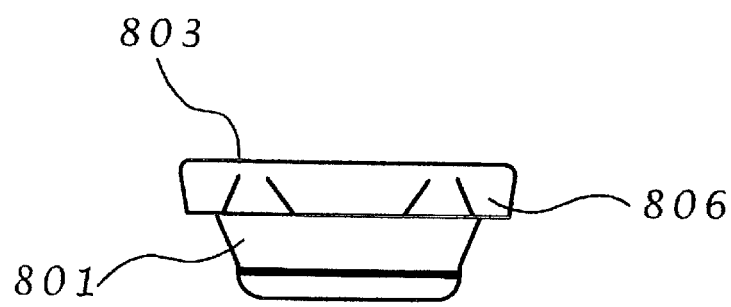
FIG. 38 is a side view of the swaged dosage form.
Figure 39:
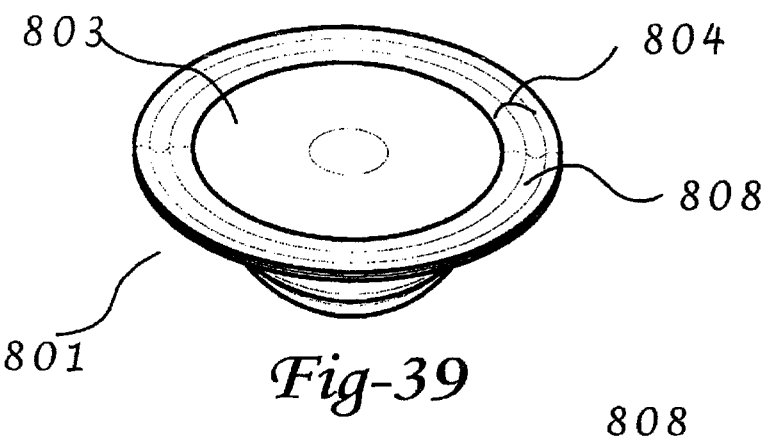
FIG. 39 is a view of a dosage form with a sealing depression around the sealing area.
Figure 40:
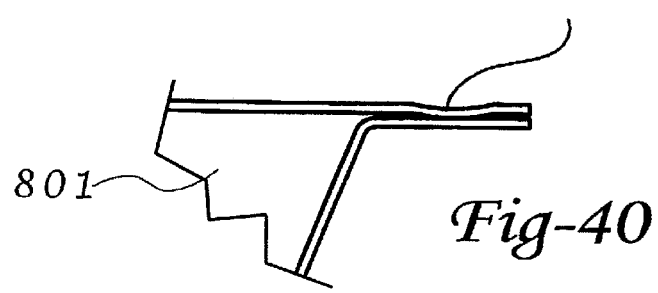
FIGS. 40-42 are side views of embodiments of the dosage form as shown in FIG. 39.
Figures 41, 42:
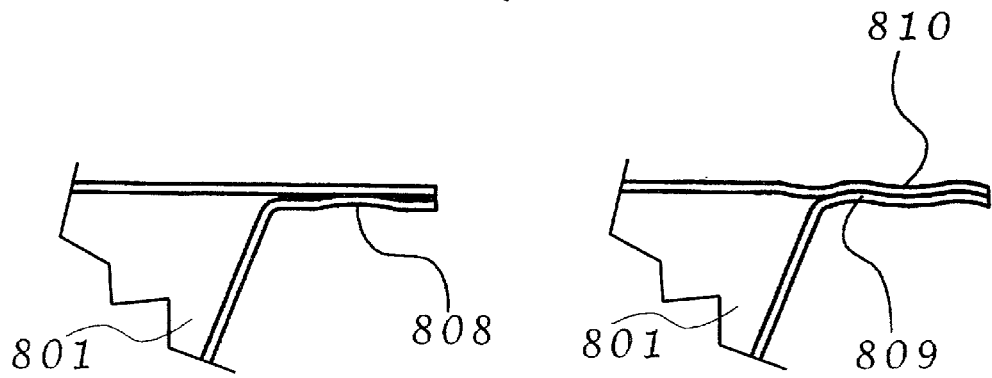

Another embodiment of a dual chamber dosage form that provides a greater degree of mixing of the two components is shown in FIG. 32. This embodiment 751 includes a first dosage chamber 728, a first delamination zone 731, a second dosage chamber 729, a curved or serpentine delamination zone 752 and a dispensing chamber 730. Pressure on the diaphragm of first dosage chamber 728 causes the separation of first delamination zone 731 and flow of the first agent into the second dosage chamber 729. Further pressure causes separation of the curved or serpentine delamination zone 752 and flow of the agent through the delamination zone 752 into and through the dispensing chamber 730. The turns in the delamination zone 752 increase the mixing of the components. Additional mixing means can also be employed such as restrictions in the flow path, separation into multiple flow paths, or other methods known to those of skill in the art.

Since the rate and method of absorption of various fluid or solid agents are influenced by the droplet size and distribution inside the nasal cavity, it is beneficial to control this spray pattern. The surface features 74 can be designed for different types of spiral, vertical and other flow and the design can be adjusted for different viscosities of the fluid or solid to be dispensed. For example, surface features may be added to create a vortex, to further mix the contents of the blister, to change the fluid property type from laminar to turbulent or vice versa or to change fluid properties such as pressure, velocity, surface tension or viscosity. This use of surface features to control spray pattern can also be applied to the discharge passage 55 of the piercing body 54 of the positive displacement dosage form 50 described earlier.

In certain embodiments, a shaped blister dosage form as described herein that contains medication and an internal piercing nozzle, is configured for use in a smaller diameter dispensing mechanism, while still providing an accurate dose of medicine in the form of a controlled spray. A blister strip 800 including a plurality of such dosage forms 801 is shown in FIG. 33. The strips include a blister material layer 802 in which the dosage forms are formed, and a lid material 803 (shown on the reverse side of the strip in FIG. 34) bonded to the blister material. A concentric sealing area 804 provides a resilient seal that is not broken when the dosage forms are crushed to deliver the contained medication.

To successfully dispense the medication, the medication must flow through the piercing nozzle with enough velocity to create the desired spray geometry. As described herein, this is accomplished by pressing on the blister form with sufficient force to push the piercing nozzle through the lid material, completely crushing the dosage form and forcing the contents through the nozzle with the required velocity. During this dispensing operation, the seal of the lid material to the blister material must be strong enough that no leakage occurs prior to the nozzle piercing the lid. The smaller size required by certain dosage situations, such as intranasal administration present greater challenges to the seal of the lid material to the blister material.

A trimmed dosage form is shown in FIG. 35 in which a trim edge 805 is shown outside the sealing area 804, providing a smaller diameter dosage form for certain uses. A side view of the dosage form is shown in FIG. 36. The dosage form can also be swaged or pressure formed in a way to further reduce the overall diameter without negatively impacting the strength of the seal of the lid material to the blister material. A swaged dosage form is shown in FIG. 37. In the swaged dosage form the rim 806 is formed to further reduce the outside diameter 807.

In certain embodiments, as shown in FIG. 39, the strength of the seal area 804 can be increased by forming a concentric depression 808 around the seal area 804. As shown in side vie in FIGS. 40-42, a depression can be formed in the lid material (FIG. 40), in the blister material (FIG. 41) or in both (FIG. 42).

All of the devices and methods disclosed and claimed herein can be made and executed without undue experimentation in light of the present disclosure. While the devices and methods of this invention have been described in terms of preferred embodiments, it will be apparent to those of skill in the art that variations may be applied to the devices and/or methods and in the steps or in the sequence of steps of the methods described herein without departing from the concept, spirit and scope of the invention. All such similar substitutes and modifications apparent to those skilled in the art are deemed to be within the spirit, scope and concept of the invention as defined by the appended claims.

The invention claimed is:

1. An internally pierced formed blister comprising:

a blister formed from a stretched flexible film material into a recess with an open end;

a piercable surface sealed to the open end of the blister to form an internal chamber enclosed by the formed recess; and a piercing nozzle wholly contained in the internal chamber, the piercing nozzle comprising a base, a tapered hollow elongated body, projecting from the base at a first end, and forming an internal channel and a discharge nozzle at a second end opposite the base, and comprising structural features on the surface of the internal channel to control the spray pattern and droplet size of a fluid forced to flow through the piercing nozzle under pressure, and one or more inlet openings and channels providing a fluid path from the internal chamber through the base and into the internal channel of the piercing nozzle and out the discharge nozzle.

2. The internally pierced formed blister of claim 1, wherein the structural features include contours, steps, flutes, ribs, constrictions, or a combination thereof.

3. The internally pierced formed blister of claim 1, wherein the fluid path from the internal chamber into the internal channel comprises one or more bends.

4. The internally pierced formed blister of claim 3, wherein the one or more bends include at least one 90° bend.

5. The internally pierced formed blister of claim 1, wherein the fluid path and structural features produce a vortex in fluids forced through the piercing nozzle under pressure.

6. The internally pierced formed blister of claim 1, wherein the piercing nozzle is held in position in the internal chamber by a close fit of the base with the shape of the recess opposite the piercable surface and wherein the position includes the discharge nozzle proximate the piercable surface.

7. The internally pierced formed blister of claim 1, further comprising a liquid or powdered composition contained in the internal chamber.

8. The internally pierced formed blister of claim 7, wherein the composition and the internal chamber are sterile.

9. The internally pierced formed blister of claim 7, wherein the composition is a medical composition.

* * * * *